(12) United States Patent
Shapiro et al.

(10) Patent No.: US 11,144,378 B2
(45) Date of Patent: Oct. 12, 2021

(54) COMPUTER SYSTEM AND METHOD FOR RECOMMENDING AN OPERATING MODE OF AN ASSET

(71) Applicant: Uptake Technologies, Inc., Chicago, IL (US)

(72) Inventors: Stephanie Shapiro, Chicago, IL (US); Brian Silva, Chicago, IL (US)

(73) Assignee: Uptake Technologies, Inc., Chicago, IL (US)

( * ) Notice: Subject to any disclaimer, the term of this patent is extended or adjusted under 35 U.S.C. 154(b) by 170 days.

(21) Appl. No.: 16/125,335

(22) Filed: Sep. 7, 2018

(65) Prior Publication Data

US 2019/0003929 A1  Jan. 3, 2019
US 2020/0278273 A9  Sep. 3, 2020

Related U.S. Application Data

(63) Continuation-in-part of application No. 14/732,285, filed on Jun. 5, 2015, now Pat. No. 10,176,032.

(51) Int. Cl.
*G01M 99/00* (2011.01)
*G06F 11/07* (2006.01)
(Continued)

(52) U.S. Cl.
CPC ............. *G06F 11/079* (2013.01); *G01D 3/08* (2013.01); *G01M 99/005* (2013.01);
(Continued)

(58) Field of Classification Search
CPC . G01M 99/005; G05B 19/18; G05B 23/0254; G05B 23/0275; G07C 5/08;
(Continued)

(56) References Cited

U.S. PATENT DOCUMENTS 3,026,510 A  3/1962  Davis
5,079,691 A  1/1992  Heck et al.
(Continued)

FOREIGN PATENT DOCUMENTS

CN  102045181       5/2011
CN  104398431 A     3/2015
(Continued)

OTHER PUBLICATIONS

Biswas, "Redundancy-based Approaches in Wireless Multihop Network Design", PhD Dissertation Submitted to Graduate Faculty of North Carolina State University (2014).
(Continued)

*Primary Examiner* — Michael P Nghiem
(74) *Attorney, Agent, or Firm* — Lee Sullivan Shea & Smith LLP

(57) ABSTRACT

Disclosed herein are systems, devices, and methods related to assets and asset operating conditions. In particular, examples involve determining health metrics that estimate the operating health of an asset or a part thereof, determining recommended operating modes for assets, analyzing health metrics to determine variables that are associated with high health metrics, and modifying the handling of operating conditions that normally result in triggering of abnormal-condition indicators, among other examples.

20 Claims, 14 Drawing Sheets

(51) Int. Cl.

| | | |
|---|---|---|
| *G06F 11/00* | (2006.01) | |
| *G05B 23/02* | (2006.01) | |
| *G06Q 10/00* | (2012.01) | |
| *G06Q 50/04* | (2012.01) | |
| *G06Q 50/08* | (2012.01) | |
| *G06Q 10/06* | (2012.01) | |
| *G05B 19/18* | (2006.01) | |
| *G07C 5/00* | (2006.01) | |
| *G07C 5/08* | (2006.01) | |
| *G06F 11/26* | (2006.01) | |
| *G06F 11/263* | (2006.01) | |
| *G08B 21/18* | (2006.01) | |
| *G01D 3/08* | (2006.01) | |
| *G06F 11/20* | (2006.01) | |
| *G06N 5/02* | (2006.01) | |
| *G06N 7/00* | (2006.01) | |
| *H04L 12/707* | (2013.01) | |
| *G06N 5/04* | (2006.01) | |
| *G06Q 10/04* | (2012.01) | |

(52) U.S. Cl.
CPC .......... *G01M 99/008* (2013.01); *G05B 19/18* (2013.01); *G05B 23/0254* (2013.01); *G05B 23/0275* (2013.01); *G06F 11/008* (2013.01); *G06F 11/0709* (2013.01); *G06F 11/0721* (2013.01); *G06F 11/0751* (2013.01); *G06F 11/0754* (2013.01); *G06F 11/0772* (2013.01); *G06F 11/0787* (2013.01); *G06F 11/0793* (2013.01); *G06F 11/2007* (2013.01); *G06F 11/26* (2013.01); *G06F 11/263* (2013.01); *G06N 5/02* (2013.01); *G06N 5/04* (2013.01); *G06N 7/005* (2013.01); *G06Q 10/04* (2013.01); *G06Q 10/067* (2013.01); *G06Q 10/0633* (2013.01); *G06Q 10/06312* (2013.01); *G06Q 10/20* (2013.01); *G06Q 50/04* (2013.01); *G06Q 50/08* (2013.01); *G07C 5/008* (2013.01); *G07C 5/0808* (2013.01); *G07C 5/0825* (2013.01); *G08B 21/18* (2013.01); *H04L 45/22* (2013.01); *G06F 2201/85* (2013.01)

(58) Field of Classification Search
CPC . G07C 5/0808; G07C 5/0825; G06F 11/2007; G06F 11/079
USPC .......................................... 702/184
See application file for complete search history.

(56) References Cited

U.S. PATENT DOCUMENTS

| | | | |
|---|---|---|---|
| 5,363,317 | A | 11/1994 | Rice |
| 5,566,092 | A | 10/1996 | Wang et al. |
| 5,633,800 | A | 5/1997 | Bankert et al. |
| 5,918,222 | A | 6/1999 | Fukui |
| 6,115,697 | A | 9/2000 | Gottstein |
| 6,336,065 | B1 | 1/2002 | Gibson et al. |
| 6,442,542 | B1 | 8/2002 | Ramani et al. |
| 6,473,659 | B1 | 10/2002 | Shah et al. |
| 6,622,264 | B1 | 9/2003 | Bliley et al. |
| 6,625,500 | B1 | 9/2003 | Li |
| 6,634,000 | B1 | 10/2003 | Jammu et al. |
| 6,643,600 | B2 | 11/2003 | Yanosik et al. |
| 6,650,949 | B1 | 11/2003 | Fera et al. |
| 6,708,156 | B1 | 3/2004 | Gonten |
| 6,725,398 | B1 | 4/2004 | Varma et al. |
| 6,760,631 | B1 | 7/2004 | Berkowitz et al. |
| 6,775,641 | B2 | 8/2004 | Wegerich et al. |
| 6,799,154 | B1 | 9/2004 | Aragones et al. |
| 6,823,253 | B2 | 11/2004 | Brunell |
| 6,859,739 | B2 | 2/2005 | Wegerich et al. |
| 6,892,163 | B1 | 5/2005 | Herzog et al. |
| 6,947,797 | B2 | 9/2005 | Dean et al. |
| 6,952,662 | B2 | 10/2005 | Wegerich et al. |
| 6,957,172 | B2 | 10/2005 | Wegerich |
| 6,975,962 | B2 | 12/2005 | Wegerich et al. |
| 7,020,595 | B1 | 3/2006 | Adibhatla et al. |
| 7,082,379 | B1 | 7/2006 | Bickford et al. |
| 7,100,084 | B2 | 8/2006 | Unkle et al. |
| 7,107,491 | B2 | 9/2006 | Graichen et al. |
| 7,127,371 | B2 | 10/2006 | Duckert et al. |
| 7,158,917 | B1 | 1/2007 | Bickford |
| 7,174,233 | B1 | 2/2007 | Blackshear et al. |
| 7,233,886 | B2 | 6/2007 | Wegerich et al. |
| 7,280,941 | B2 | 10/2007 | Bonanni et al. |
| 7,308,385 | B2 | 12/2007 | Wegerich et al. |
| 7,373,283 | B2 | 5/2008 | Herzog et al. |
| 7,403,869 | B2 | 7/2008 | Wegerich et al. |
| 7,409,320 | B2 | 8/2008 | Wegerich |
| 7,415,382 | B1 | 8/2008 | Bickford et al. |
| 7,428,478 | B2 | 9/2008 | Aragones |
| 7,447,666 | B2 | 11/2008 | Wang |
| 7,457,693 | B2 | 11/2008 | Olsen et al. |
| 7,457,732 | B2 | 11/2008 | Aragones et al. |
| 7,509,235 | B2 | 3/2009 | Bonissone et al. |
| 7,536,364 | B2 | 5/2009 | Subbu et al. |
| 7,539,597 | B2 | 5/2009 | Wegerich et al. |
| 7,548,830 | B2 | 6/2009 | Goebel et al. |
| 7,599,762 | B2 | 10/2009 | Discenzo |
| 7,634,384 | B2 | 12/2009 | Eryurek et al. |
| 7,640,145 | B2 | 12/2009 | Wegerich et al. |
| 7,660,705 | B1 | 2/2010 | Meek et al. |
| 7,725,293 | B2 | 5/2010 | Bonissone et al. |
| 7,729,789 | B2 | 6/2010 | Blevins |
| 7,739,096 | B2 | 6/2010 | Wegerich et al. |
| 7,756,678 | B2 | 7/2010 | Bonissone et al. |
| 7,822,578 | B2 | 10/2010 | Kasztenny et al. |
| 7,869,908 | B2 | 1/2011 | Walker |
| 7,919,940 | B2 | 4/2011 | Miller et al. |
| 7,941,701 | B2 | 5/2011 | Wegerich et al. |
| 7,962,240 | B2 | 6/2011 | Morrison et al. |
| 8,024,069 | B2 | 9/2011 | Miller et al. |
| 8,050,800 | B2 | 11/2011 | Miller et al. |
| 8,135,481 | B2 | 3/2012 | Blevins |
| 8,145,578 | B2 | 3/2012 | Pershing et al. |
| 8,229,769 | B1 | 7/2012 | Hopkins |
| 8,234,420 | B2 | 7/2012 | Lueckenbach et al. |
| 8,239,170 | B2 | 8/2012 | Wegerich |
| 8,275,577 | B2 | 9/2012 | Herzog |
| 8,285,402 | B2 | 10/2012 | Lueckenbach et al. |
| 8,311,774 | B2 | 11/2012 | Hines |
| 8,352,216 | B2 | 1/2013 | Subbu et al. |
| 8,532,795 | B2 | 9/2013 | Adavi et al. |
| 8,533,018 | B2 | 9/2013 | Miwa et al. |
| 8,560,494 | B1 | 10/2013 | Downing et al. |
| 8,620,618 | B2 | 12/2013 | Eryurek et al. |
| 8,620,853 | B2 | 12/2013 | Herzog |
| 8,626,385 | B2 | 1/2014 | Humphrey |
| 8,645,276 | B2 | 2/2014 | Wong et al. |
| 8,660,980 | B2 | 2/2014 | Herzog |
| 8,682,454 | B2 | 3/2014 | Fuller |
| 8,689,108 | B1 | 4/2014 | Duffield et al. |
| 8,713,467 | B1 | 4/2014 | Goldenberg et al. |
| 8,786,605 | B1 | 7/2014 | Curtis et al. |
| 8,799,799 | B1 | 8/2014 | Cervelli et al. |
| 8,812,960 | B1 | 8/2014 | Sun et al. |
| 8,825,567 | B2 | 9/2014 | Jiang et al. |
| 8,832,594 | B1 | 9/2014 | Thompson et al. |
| 8,850,000 | B2 | 9/2014 | Collins et al. |
| 8,862,938 | B2 | 10/2014 | Souvannarath |
| 8,868,537 | B1 | 10/2014 | Colgrove et al. |
| 8,886,601 | B1 | 11/2014 | Landau et al. |
| 8,909,656 | B2 | 12/2014 | Kumar et al. |
| 8,917,274 | B2 | 12/2014 | Ma et al. |
| 8,918,246 | B2 | 12/2014 | Friend |
| 8,924,429 | B1 | 12/2014 | Fisher et al. |
| 8,935,201 | B1 | 1/2015 | Fisher et al. |
| 8,937,619 | B2 | 1/2015 | Sharma et al. |
| 8,938,686 | B1 | 1/2015 | Erenrich et al. |

(56) References Cited

U.S. PATENT DOCUMENTS

| | | | |
|---|---|---|---|
| 9,007,896 B2 | 4/2015 | North | |
| 9,260,976 B2 | 2/2016 | Phillips | |
| 9,471,452 B2 | 10/2016 | McElhinney | |
| 9,864,665 B2 | 1/2018 | McElhinney | |
| 10,176,032 B2 * | 1/2019 | Horrell | G06Q 50/04 |
| 10,417,076 B2 * | 9/2019 | Ciasulli | G06F 11/008 |
| 2002/0059075 A1 | 5/2002 | Schick et al. | |
| 2002/0091972 A1 * | 7/2002 | Harris | G06F 11/008 714/47.2 |
| 2002/0152056 A1 | 10/2002 | Herzog et al. | |
| 2003/0055666 A1 | 3/2003 | Roddy et al. | |
| 2003/0065555 A1 | 4/2003 | von Gonton et al. | |
| 2003/0126258 A1 | 7/2003 | Conkright et al. | |
| 2003/0130883 A1 | 7/2003 | Schroeder et al. | |
| 2004/0181712 A1 | 9/2004 | Taniguchi et al. | |
| 2004/0243636 A1 | 12/2004 | Hasiewicz et al. | |
| 2005/0119905 A1 | 6/2005 | Wong et al. | |
| 2005/0222747 A1 | 10/2005 | Vhora et al. | |
| 2006/0036403 A1 | 2/2006 | Wegerich et al. | |
| 2006/0048018 A1 | 3/2006 | Hosoya et al. | |
| 2006/0293777 A1 | 12/2006 | Breitgand | |
| 2007/0005266 A1 * | 1/2007 | Blevins | G06Q 50/04 702/22 |
| 2007/0050115 A1 | 3/2007 | Discenzo | |
| 2007/0088570 A1 | 4/2007 | Shetty | |
| 2007/0263628 A1 | 11/2007 | Axelsson et al. | |
| 2007/0266557 A1 | 11/2007 | Drost et al. | |
| 2007/0288414 A1 | 12/2007 | Barajas et al. | |
| 2008/0040244 A1 | 2/2008 | Ricciuti et al. | |
| 2008/0059080 A1 | 3/2008 | Greiner et al. | |
| 2008/0059120 A1 | 3/2008 | Xiao et al. | |
| 2008/0097945 A1 | 4/2008 | Greis et al. | |
| 2008/0255760 A1 | 10/2008 | Rojicek et al. | |
| 2009/0006373 A1 * | 1/2009 | Chakrabarti | G06F 16/335 |
| 2009/0240636 A1 | 9/2009 | Hofmann et al. | |
| 2009/0326890 A1 | 12/2009 | Shetty | |
| 2010/0023239 A1 | 1/2010 | Self | |
| 2010/0114423 A1 | 5/2010 | Boss et al. | |
| 2010/0222899 A1 | 9/2010 | Blevins | |
| 2011/0080828 A1 | 4/2011 | North | |
| 2011/0276828 A1 | 11/2011 | Tamaki et al. | |
| 2012/0190342 A1 | 7/2012 | Seibert | |
| 2012/0221156 A1 | 8/2012 | Fuller | |
| 2012/0271612 A1 | 10/2012 | Barsoum et al. | |
| 2012/0310597 A1 | 12/2012 | Uchiyama et al. | |
| 2013/0010610 A1 | 1/2013 | Karthikeyan et al. | |
| 2013/0024416 A1 | 1/2013 | Herzog | |
| 2013/0063262 A1 | 3/2013 | Shaikh et al. | |
| 2013/0204808 A1 | 8/2013 | Jiang et al. | |
| 2013/0283773 A1 | 10/2013 | Hague | |
| 2013/0325502 A1 | 12/2013 | Robicsek et al. | |
| 2014/0012886 A1 | 1/2014 | Downing et al. | |
| 2014/0032132 A1 | 1/2014 | Stratton et al. | |
| 2014/0060030 A1 | 3/2014 | Ma et al. | |
| 2014/0089035 A1 | 3/2014 | Jericho et al. | |
| 2014/0105481 A1 | 4/2014 | Hasselbusch et al. | |
| 2014/0121868 A1 | 5/2014 | Zhang et al. | |
| 2014/0164851 A1 | 6/2014 | Pelly et al. | |
| 2014/0169398 A1 | 6/2014 | Arndt et al. | |
| 2014/0170617 A1 | 6/2014 | Johnson et al. | |
| 2014/0184643 A1 | 7/2014 | Friend | |
| 2014/0199219 A1 | 7/2014 | Christner et al. | |
| 2014/0222355 A1 | 8/2014 | Cheim et al. | |
| 2014/0271114 A1 | 9/2014 | Phillips | |
| 2014/0330600 A1 | 11/2014 | Candas et al. | |
| 2014/0330749 A1 | 11/2014 | Candas et al. | |
| 2014/0351642 A1 | 11/2014 | Bates et al. | |
| 2014/0357295 A1 | 12/2014 | Skomra et al. | |
| 2014/0358601 A1 | 12/2014 | Smiley et al. | |
| 2014/0365191 A1 | 12/2014 | Zyglowicz | |
| 2014/0365271 A1 | 12/2014 | Smiley | |
| 2015/0037898 A1 | 2/2015 | Baldus et al. | |
| 2015/0046870 A1 | 2/2015 | Goldenberg et al. | |
| 2015/0112903 A1 | 4/2015 | Chan et al. | |
| 2015/0160098 A1 | 6/2015 | Noda | |
| 2015/0262060 A1 | 9/2015 | Husain et al. | |
| 2015/0301882 A1 | 10/2015 | Liao et al. | |
| 2016/0012707 A1 | 1/2016 | McKinley et al. | |
| 2016/0055737 A1 | 2/2016 | Boken | |
| 2016/0078695 A1 | 3/2016 | McClintic et al. | |
| 2016/0153806 A1 * | 6/2016 | Ciasulli | G06Q 10/067 702/184 |
| 2016/0154690 A1 * | 6/2016 | Horrell | G05B 23/0254 714/57 |
| 2016/0155098 A1 | 6/2016 | McElhinney | |
| 2016/0155315 A1 | 6/2016 | McElhinney | |
| 2016/0349330 A1 | 12/2016 | Barfield, Jr. et al. | |
| 2016/0359683 A1 | 12/2016 | Bartfai-Walcott et al. | |
| 2016/0371584 A1 | 12/2016 | Nicholas | |
| 2016/0371585 A1 | 12/2016 | McElhinney | |
| 2016/0379465 A1 | 12/2016 | McElhinney | |
| 2018/0060832 A1 | 3/2018 | Korsedal, IV et al. | |

FOREIGN PATENT DOCUMENTS

| | | |
|---|---|---|
| EP | 3026510 | 6/2016 |
| GB | 2491291 A | 8/2012 |
| JP | H06162300 A | 6/1994 |
| JP | 2000315111 | 11/2000 |
| JP | 20100113672 A | 5/2010 |
| JP | 2011201336 A | 10/2011 |
| JP | 2012133672 | 7/2012 |
| KR | 1020180006893 | 1/2018 |
| WO | 2002054223 | 7/2002 |
| WO | 2011117570 | 9/2011 |
| WO | 2013034420 | 3/2013 |
| WO | 2014054051 | 4/2014 |
| WO | 2014145977 | 9/2014 |
| WO | 2014205497 | 12/2014 |

OTHER PUBLICATIONS

Isermann, "Model-based Fault Detection and Diagnosis—Status and Applications", Institute of Automatic Control, Darmstadt University of Technology (2004).

Narasimhan et al, "Combining Model-Based and Feature-Driven Diagnosis Approaches—A Case Study on Electromechanical Actuators", 21st International Workshop on Principles of Diagnosis (2010).

Prentzas et al, Categorizing Approaches Combining Rule-Based and Case-Based Reasoning.

Infor M3 Enterprise Management System, Infor.com (2014).

Infor Equipment, Infor.com (2012).

Infor Introduces Next-Generation Solution for Equipment Dealers and Service Providers, Infor.com (Feb. 20, 2014).

Infor Equipment for Rental, Infor.com (2013).

Waltermire et al, Applying the Continuous Monitoring Technical Reference Model to the Asset, Configuration, and Vulnerability Management Domains (DRAFT), NIST (Jan. 2012).

European Patent Office Extended Search Report for EP Application No. 15866135.5 dated Apr. 23, 2018, 9 pages.

Intellectial Property Office of Singapore , Written Opinion dated Jan. 18, 2018, issued in connection with Singapore Application No. 11201708094X, filed on Oct. 2, 2017, 8 pages.

International Search Report for Application No. PCT/US2015/063047, dated Mar. 28, 2016, 3 pages.

Duan et al. "Short Paper: Data Mining-based Fault Prediction and Detection on the Grid" High Performance Distributed Computing, 2006 15th IEEE International Symposium on IEEE, 4 pages.

International Searching Authority, Written Opinion dated Mar. 28, 2016, issued in connection with International Application No. PCT/US2015/063047, filed on Nov. 30, 2015, 8 pages.

European Patent Office Examination Report for EP Application No. 15866135.5 dated Jun. 5, 2019, 8 pages.

Biswas, Trisha. Redundancy-based Approaches in Wireless Multihop Network Design. PhD Dissertation Submitted to Graduate Faculty of North Carolina State University, Raleigh, North Carolina, Mar. 25, 2014, pp. 1-141 [online], [originally retrieved on May 26, 2015].

(56) References Cited

OTHER PUBLICATIONS

Retrieved from the Internet <URL:https://repository.lib.ncsu.edu/bitstream/handle/1840.16/9313/etd.pdf?sequence=2&isAllowed=y>.

Isermann, Rolf. Model-based Fault Detection and Diagnosis—Status and Applications. Institute of Automatic Control, Darmstadt University of Technology, Darmstadt, Germany, Jun. 2004, pp. 1-12.[online], [originally retrieved on Oct. 8, 2015]. Retrieved from the Internet <URL: http://citeseerx.ist.psu.edu/viewdoc/download?doi=10.1.1.113.9295&rep=rep1&type=pdf>.

Narasimhan et al. Combining Model-Based and Feature-Driven Diagnosis Approaches—A Case Study on Electromechanical Actuators. 21st International Workshop on Principles of Diagnosis 2010, pp. 1-8. [online], [originally retrieved on Oct. 8, 2015] Retrieved from the Internet <URL:https://ti.arc.nasa.gov/publications/2266/download/>.

Prentzas et al. Categorizing Approaches Combining Rule-Based and Case-Based Reasoning. Expert Systems 24, Apr. 17, 2007, pp. 1-34 [online], [originally retrieved on Oct. 8, 2015]. Retrieved from the Internet <URL:http://citeseerx.ist.psu.edu/viewdoc/download?doi=10.1.1.143.2780&rep=rep1&type=pdf>.

Infor M3 Enterprise Management System. Datasheet [online]. Infor, 2014 [originally retrieved May 19, 2015]. Retrieved from the Internet: <URL:www.infor.com.html>.

Infor Equipment. Datasheet [online]. Infor, 2012 [originally retrieved May 19, 2015]. Retrieved from the Internet<URL: www.infor.com.html>.

Infor Introduces Next-Generation Solution for Equipment Dealers and Service Providers. Infor, Feb. 2014 pp. 1-5. [online], [originally retrieved May 19, 2015]. Retrieved from the Internet<URL:www.infor.com/company/news/pressroom/pressreleases/M3equipment.html>.

Infor Equipment for Rental. Datasheet [online] Infor, 2013 [originally retrieved May 19, 2015]. Retrieved from the Internet: <URL:www.infor.com.html>.

Waltermire et al. Applying the Continuous Monitoring Technical Reference Model to the Asset, Configuration, and Vulnerability Management Domains (Draft). National Institute of Standards and Technology, U.S. Department of Commerce, Jan. 2012, pp. 1-23 [online], [originally retrieved Oct. 6, 2015]. Retrieved from the Internet: URL<https://csrc.nist.gov/CSRC/media/Publications/nistir/7800/draft/documents/Draft-NISTIR-7800.pdf.

Duan et al. "Short Paper: Data Mining-based Fault Prediction and Detection on the Grid" High Performance Distributed Computing, Jun. 19-23, 2006 15th IEEE International Symposium on IEEE. Retrieved from the Internet: <https://ieeexplore.ieee.org/document/1652162>.

Japanese Patent Office, Office Action and translation dated Aug. 27, 2019, issued in connection with Japanese Patent Application No. 2017-547925, 4 pages.

Chinese Patent Office, First Office Action and translation dated Feb. 6, 2020 issued in connection with Chinese Application No. 201580073123.0, 12 pages.

International Searching Authority, International Search Report and Written Opinion dated Dec. 20, 2019, issued in connection with International Application No. PCT/US2019/050052, filed on Sep. 6, 2019, 11 pages.

Australian Patent Office, Examination Report dated Dec. 11, 2020 issued in connection with Australian Application No. 2015355154, 6 pages.

Alexander, Jeffrey A. et al. Methods and Metrics Challenges of Delivery-System Research. Implementation Science 2012, 10 pages.

\* cited by examiner

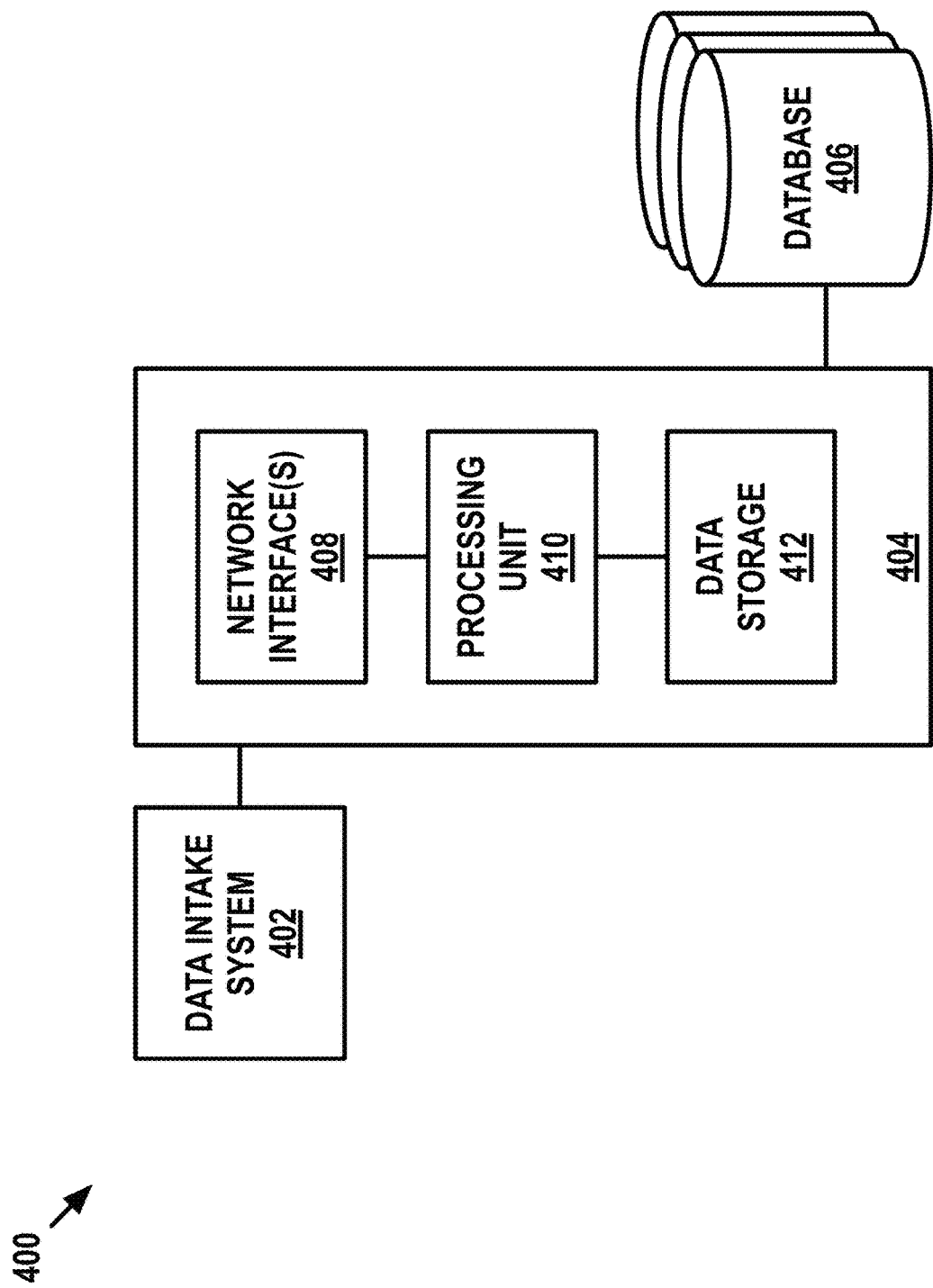

Summary

| | | | |
|---|---|---|---|
| 189 | 399 | 283 | 0.02 |
| Assets | Pending Results | Open Work Items | RFLY |

(EXPORT) (SETTINGS) (FILTERS ▽)

Assets

| | Asset ID | Pending Faults | Operational Guidance ▽ | Failure Mode | Date Last Logged | Location |
|---|---|---|---|---|---|---|
| ☐ | Asset # 6440 | 17 | Inoperable | starter | 2018-06-30 17:46:07(+00:00) | San Francisco, CA, USA |
| ☐ | Asset # 6429 | 15 | Inoperable | SlipRings | 2018-06-30 17:49:45(+00:00) | Los Angeles, CA, USA |
| ☐ | Asset # 6474 | 15 | Inoperable | battery | 2018-06-30 17:44:24(+00:00) | San Jose, CA, USA |
| ☐ | Asset # 6337 | 10 | Inoperable | battery | 2018-06-30 17:45:12(+00:00) | Palo Alto, CA, USA |
| ☐ | Asset # 6348 | 10 | Trail Only | radar | 2018-06-30 17:41:52(+00:00) | San Francisco, CA, USA |
| ☐ | Asset # 6358 | 10 | Trail Only | radar | 2018-06-30 16:46:20(+00:00) | Los Angeles, CA, USA |
| ☐ | Asset # 6423 | 9 | Trail Only | radar | 2018-06-30 13:04:19(+00:00) | San Jose, CA, USA |
| ☐ | Asset # 6427 | 8 | Limited Use | wheel | 2018-06-30 17:57:44(+00:00) | Palo Alto, CA, USA |
| ☐ | Asset # 6371 | 8 | Limited Use | injector | 2018-06-30 16:47:52(+00:00) | San Francisco, CA, USA |
| ☐ | Asset # 6467 | 7 | Limited Use | fan | 2018-06-30 17:49:44(+00:00) | Los Angeles, CA, USA |
| ☐ | Asset # 6334 | 7 | Full Operation | Sensor | 2018-06-30 11:37:42(+00:00) | San Jose, CA, USA |
| ☐ | Asset # 6357 | 7 | , | , | 2018-06-30 03:47:30(+00:00) | Palo Alto, CA, USA |
| ☐ | Asset # 6475 | 7 | , | , | 2018-06-30 17:55:07(+00:00) | San Francisco, CA, USA |
| ☐ | Asset # 6478 | 6 | , | , | 2018-06-30 16:27:03(+00:00) | Los Angeles, CA, USA |

FIG. 9A

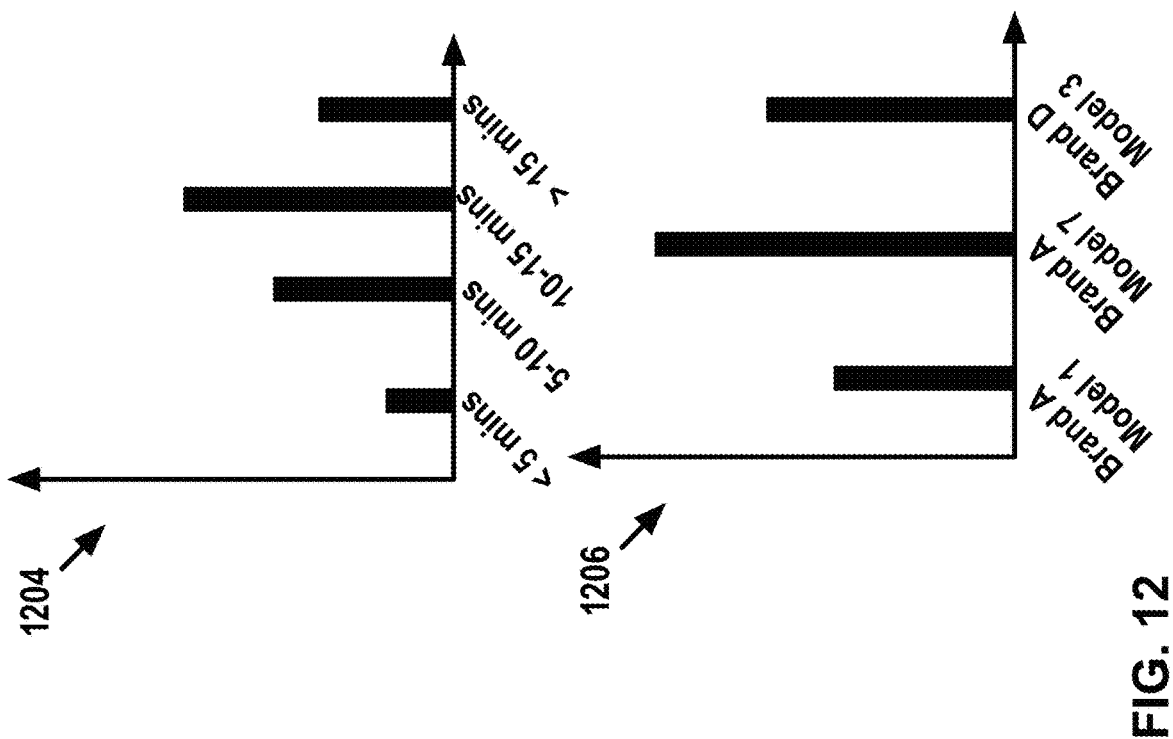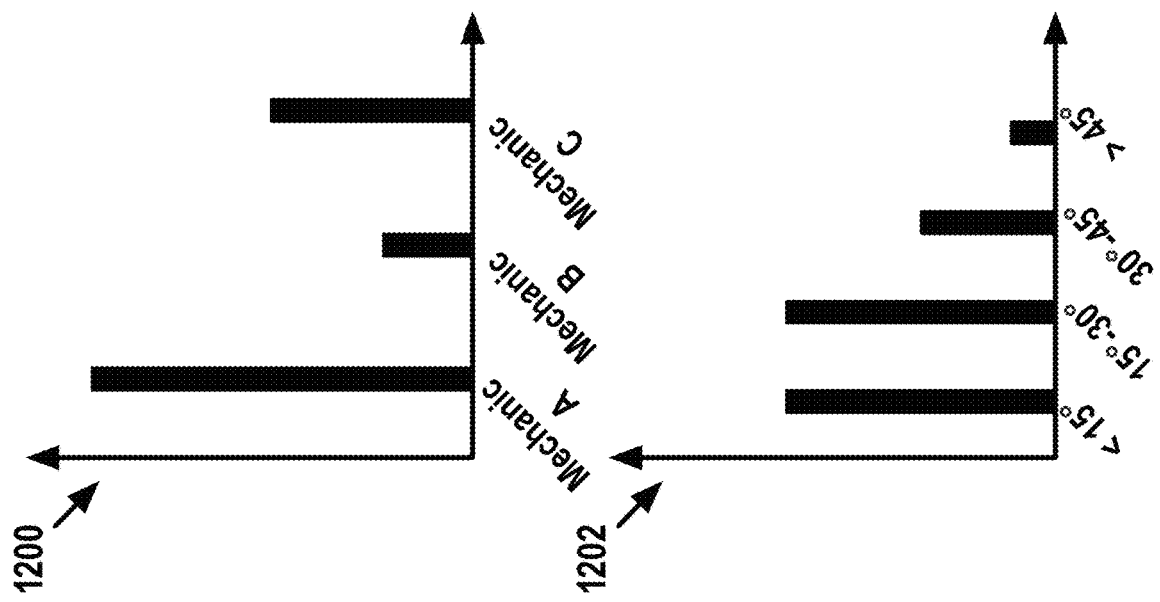
FIG. 12

COMPUTER SYSTEM AND METHOD FOR RECOMMENDING AN OPERATING MODE OF AN ASSET

CROSS REFERENCE TO RELATED APPLICATIONS

This application claims priority to and is a continuation-in-part of U.S. Non-Provisional patent application Ser. No. 14/732,285, which was filed on Jun. 5, 2015, is entitled "Subsystem Health Score," and issued as U.S. Pat. No. 10,176,032 on Jan. 8, 2019. In addition, this application hereby incorporates by reference each of the following U.S. patent applications in its entirety: (i) U.S. Non-Provisional patent application Ser. No. 14/732,258, now U.S. Pat. No. 10,417,076, which was filed on Jun. 5, 2015 and is entitled "Asset Health Score," (ii) U.S. Provisional Patent Application No. 62/086,155, filed Dec. 1, 2014, entitled Method and Apparatus for Displaying Information Related to Industrial Application Health and Capability Information, and (iii) U.S. Provisional Patent Application No. 62/088,651, filed Dec. 7, 2014, entitled Uptake+CAT.

BACKGROUND

Today, machines (also referred to herein as "assets") are ubiquitous in many industries. From locomotives that transfer cargo across countries to medical equipment that helps nurses and doctors to save lives, assets serve an important role in everyday life. Depending on the role that an asset serves, its complexity, and cost, may vary. For instance, some assets may include multiple subsystems that must operate in harmony for the asset to function properly (e.g., an engine, transmission, etc. of a locomotive).

Because of the key role that assets play in everyday life, it is desirable for assets to be repairable with limited downtime. Accordingly, some have developed mechanisms to monitor and detect abnormal conditions within an asset to facilitate repairing the asset, perhaps with minimal downtime.

OVERVIEW

The current approach for monitoring assets generally involves an on-asset computer that receives signals from various sensors distributed throughout the asset that monitor operating conditions of the asset. As one representative example, if the asset is a locomotive, the sensors may monitor parameters such as temperatures, voltages, and speeds, among other examples. If sensor signals from one or more sensors reach certain values, the on-asset computer may then generate an abnormal-condition indicator, such as a "fault code," which is an indication that an abnormal condition has occurred within the asset. In practice, a user typically defines the sensors and respective sensor values associated with each abnormal-condition indicator. That is, the user defines an asset's "normal" operating conditions (e.g., those that do not trigger abnormal-condition indicators) and "abnormal" operating conditions (e.g., those that trigger abnormal-condition indicators).

In general, an abnormal condition may be a defect at an asset or component thereof, which may lead to a failure of the asset and/or component. As such, an abnormal condition may be associated with a given failure, or perhaps multiple failures, in that the abnormal condition is symptomatic of the given failure or failures.

After the on-asset computer generates an abnormal-condition indicator, the indicator and/or sensor signals may be passed to a remote location where a user may receive some indication of the abnormal condition and decide whether to take action. In some cases, the user may also review the sensor signals associated with the abnormal-condition indicator to facilitate diagnosing the cause of the abnormal-condition indicator.

While current asset-monitoring systems are generally effective at triggering abnormal-condition indicators, such systems are typically reactionary. That is, by the time the asset-monitoring system triggers an indicator, a failure within the asset may have already occurred (or is right about to occur), which may lead to costly downtime, among other disadvantages. Moreover, due to the simplistic nature of on-asset abnormality-detection mechanisms in such asset-monitoring systems, current asset-monitoring approaches tend to produce many indicators for "false positives," which may be inefficient when a user is forced to review and respond to these indicators that are not meaningful.

The example systems, devices, and methods disclosed herein seek to help address one or more of these issues. In some examples, a network configuration may include a communication network that facilitates communications between one or more assets, a remote computing system, one or more output systems, and one or more data sources.

As noted above, each asset may include multiple sensors distributed throughout the asset that facilitate monitoring operating conditions of the asset. The asset may then provide data indicative of the asset's operating conditions to the remote computing system, which may be configured to perform one or more operations based on the provided data.

In one aspect, for instance, the remote computing system may be configured to determine a health metric (also referred to herein as a "health score") of a given asset, which may be a single, aggregated parameter that reflects whether a failure will occur at the given asset within a certain period of time into the future. In example implementations, a health metric may indicate a probability that no failures from a group of failures will occur at the given asset. In other example implementations, a health metric may indicate a probability that at least one failure from a group of failures will occur at the given asset.

In general, determining a health metric may involve a "machine-learning" phase, during which the remote computing system may analyze historical operating data for one or more assets to define a model for predicting asset failures, and an asset-monitoring phase, during which the remote computing system uses a given asset's current operating data and the model defined in the machine learning phase to determine the "health score" for the given asset.

In particular, during the machine-learning phase, the remote computing system may be configured to receive operating data from one or more assets over a certain amount of time. The operating data may include sensor data, such as data reflecting the operating temperature of an engine on a locomotive, and may also include abnormal-condition indicators that were generated by the asset's on-asset computer, for instance. Based on this data, the remote computing system may be configured to determine one or more models that indicate operating conditions of the given asset that historically result in a failure at the given asset.

During the asset-monitoring phase, based on the model from the machine-learning phase and operating data from the given asset, the remote computing system may be configured to determine a probability that one or more particular failures may occur at the given asset within a preselected period of time into the future (e.g., within the next 2 weeks). In some cases, the particular failures may be "high impact" events, which are events that could cause an asset to be inoperable when they occur. From the determined failure probability, the remote computing system may determine a single, aggregated health metric for the given asset that indicates whether a failure will occur within the preselected period of time.

The remote computing system may be configured to dynamically update this health metric based on the most recent operating conditions of the given asset. That is, as the actual operating conditions of the asset change, the probability that one or more of the particular failures might occur (and thus the health metric) may change accordingly.

In particular, the remote computing system may receive operating data from the asset, perhaps in real-time. Based on the operating data and the determined model, the remote computing system may be configured to re-calculate the probability that one or more of the particular failures may occur. In the event that the probability has changed, the remote computing system may update the health metric accordingly. This process of dynamically updating the health metric may occur continuously over the course of the asset's operable life.

The remote computing system may further be configured to use the health metric to trigger a number of actions. In some cases, for instance, the remote computing system may facilitate causing an output system to output an indication of a health metric for a given asset, perhaps in conjunction with abnormal-condition indicators and/or sensor data for the given asset.

In another case, the remote computing system may be configured to generate an alert based on the health metric. For example, the remote computing system may be configured to send an alert message to an output device in the event that the health metric is approaching or has reached a health threshold, which may in turn cause the output device to output a visual and/or audible alert to the user. Other examples are also possible.

In yet another case, the remote computing system may be configured to use the health metric to trigger various types of preventative actions. For example, in the event that the health metric has reached a health threshold, the remote computing system may be configured to facilitate causing an output device to display one or more recommended actions that may affect the health metric, facilitate generating a work order to repair the asset, facilitate ordering a part for the asset, and/or transmit to the asset one or more commands that cause the asset to modify its operation. Other preventative actions are also possible.

In still another case, the remote computing system may be configured to determine a "recommended operating mode" for an asset, which is a recommendation of the particular manner in which the given asset should be used that takes into account both (1) whether any failure type of a group of failure types is predicted to occur at the asset in the foreseeable future and (2) a categorization of the particular failure type(s) that are predicted to occur in the foreseeable future (e.g., a failure severity level or other type of categorization based on safety, compliance, or the like). In other words, the "recommended operating mode" for an asset may be based not only on whether a failure is predicted to occur at an asset in the foreseeable future, but also on the categorization of the failure that is predicted to occur at the asset. In this respect, in a preferred implementation, an asset's recommended operating mode may be determined using a particular collection of multiple individual failure models (i.e., a health-metric model) that are each configured to predict a likelihood of an individual failure type in a group of failure types occurring at the given asset in the foreseeable future.

Some representative examples of a recommended operating mode may include (a) an "Inoperable" (or "Do Not Operate") mode, which represents a recommendation that an asset should not be used due to a prediction of a forthcoming failure that is expected to impact the asset's operation in a significant way, (b) a "Limited Use" mode, which represents a recommendation that an asset should only be used in a limited capacity due to a prediction of a forthcoming failure that is expected to impact the asset's operation in some meaningful way, and (c) a "Full Operation" mode, which represents a recommendation that an asset can be used at its full capacity because it is either unlikely to fail or is only likely to fail in a manner that is not expected to impact the asset's operation in a meaningful way. However, the recommended operating modes may take other forms as well— including the possibility that the recommended operating modes may be customized for particular asset types, particular industries, and/or particular end users, as examples. Likewise, it should be understood that the recommended operating modes may take different forms depending on the particular approach used for categorizing the failure types (e.g., a severity-based categorization vs. a safety-based or compliance-based categorization).

Once determined, the recommended operating mode of an asset may then be presented to an individual responsible for overseeing the asset (e.g., via a graphical user interface or the like), which may enable the individual to make a more informed decision as to how the asset should be used (e.g., whether the manner in which the asset is being used should be changed).

As described in further detail below, the remote computing system may be configured to perform various other functions as well, including determining individual "health scores" and/or recommended operating modes for respective subsystems of the given asset based on operating data from the asset, storing historical asset- and/or subsystem-level health metric and/or recommended operating mode data for assets, causing an output system to provide various visualizations based on the stored historical health metric and/or recommended operating mode data, performing analytics on stored historical health metric and/or recommended operating mode to identify certain asset-related variables that influence asset health (e.g., asset class, a mechanic that works on the asset, and environmental conditions in which the asset is operated), and/or receiving and intelligently performing operations based on feedback data from one or more output systems.

Accordingly, disclosed herein is a computing system that is programmed with the capability to perform at least the following functions: (a) receiving sensor data for a given asset, wherein the sensor data indicates operating conditions for the given asset, (b) inputting the sensor data for the given asset into a plurality of individual failure models for a group of failure types that are each configured to (1) receive the sensor data for the given asset as input and (2) output a respective value indicating a likelihood of a respective failure type occurring at the given asset within a given period of time in the future, (c) based on the respective values output by the plurality of individual failure models for the group of failure types, identifying at least one failure type that is predicted to occur at the given asset, (d) identifying a categorization of the at least one identified failure type, (e) based on the identified categorization of the at least one identified failure type, determining a recommended operating mode of the given asset, and (f) cause a computing device to display a visual representation of the recommended operating mode of the given asset.

In another aspect, disclosed herein is a non-transitory computer-readable medium, where the computer-readable medium is provisioned with software that is executable to cause a computing system to perform at least the foregoing functions.

In yet another aspect, disclosed herein is a computer-implemented method that involves at least the foregoing functions.

One of ordinary skill in the art will appreciate these as well as numerous other aspects in reading the following disclosure.

BRIEF DESCRIPTION OF THE DRAWINGS

FIG. 4 depicts a simplified block diagram of an example analytics system.

FIG. 9A depicts an example graphical user interface screen showing a listing of recommended operating modes for a plurality of assets.

FIG. 12 depicts conceptual illustrations of data that results from incrementing variable counters.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. Example Network Configuration

Figure 1:
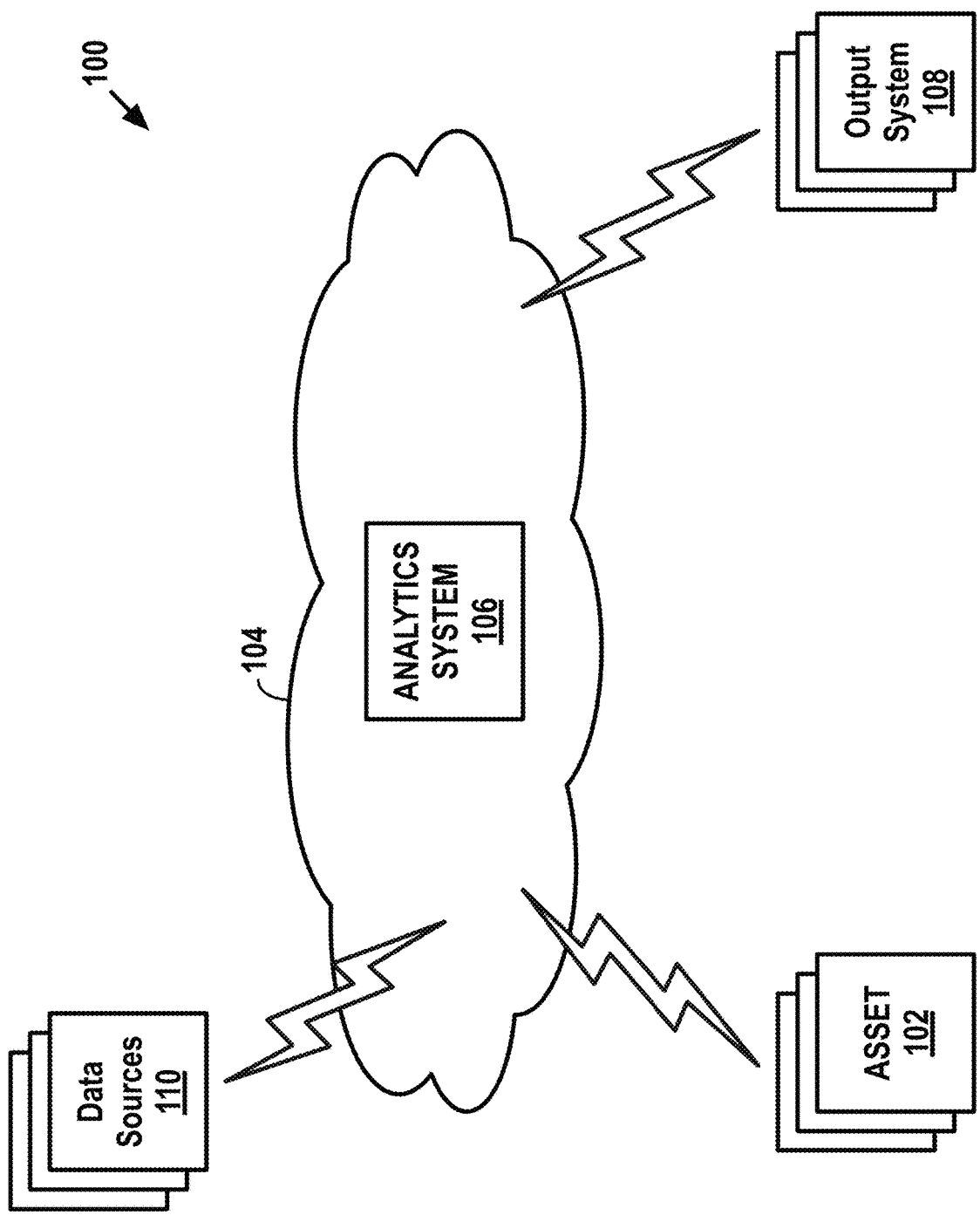
FIG. 1 depicts an example network configuration in which example embodiments may be implemented.

Turning now to the figures, FIG. 1 depicts an example network configuration 100 in which example embodiments may be implemented. As shown, the network configuration 100 includes one or more assets 102, a communication network 104, a remote computing system 106 that may take the form of an analytics system, one or more output systems 108, and one or more data sources 110.

The communication network 104 may communicatively connect each of the components in the network configuration 100. For instance, the assets 102 may communicate with the analytics system 106 via the communication network 104. In some cases, the assets 102 may communicate with one or more intermediary systems, such as a client server (not pictured), that in turn communicates with the analytics system 106. Likewise, the analytics system 106 may communicate with the output systems 108 via the communication network 104. In some cases, the analytics system 106 may communicate with one or more intermediary systems, such as a host server (not pictured), that in turn communicates with the output systems 108. Many other configurations are also possible.

In general, an asset 102 may take the form of any device configured to perform one or more operations (which may be defined based on the field) and may also include equipment configured to transmit data indicative of one or more operating conditions of the asset 102. In some examples, an asset 102 may include one or more subsystems configured to perform one or more respective operations. In practice, multiple subsystems may operate in parallel or sequentially in order for an asset 102 to operate.

Example assets may include transportation machines (e.g., locomotives, aircrafts, semi-trailer trucks, ships, etc.), industrial machines (e.g., mining equipment, construction equipment, etc.), medical machines (e.g., medical imaging equipment, surgical equipment, medical monitoring systems, medical laboratory equipment, etc.), and utility machines (e.g., turbines, solar farms, etc.), among other examples. Those of ordinary skill in the art will appreciate that these are but a few examples of assets and that numerous others are possible and contemplated herein.

In example implementations, the assets 102 shown in FIG. 1 may all be of the same type (e.g., a fleet of locomotives or aircrafts, a group of wind turbines, or a set of MRI machines, among other examples) and perhaps may be of the same class (e.g., same brand and/or model). In other examples, the assets 102 shown in FIG. 1 may differ by type, by brand, by model, etc. The assets 102 are discussed in further detail below with reference to FIG. 2.

As shown, the assets 102, and perhaps other data sources 110, may communicate with the analytics system 106 via the communication network 104. In general, the communication network 104 may include one or more computing systems and network infrastructure configured to facilitate transferring data between network components. The communication network 104 may be or may include one or more Wide-Area Networks (WANs) and/or Local-Area Networks (LANs), which may be wired and/or wireless. In some examples, the communication network 104 may include one or more cellular networks and/or the Internet, among other networks. The communication network 104 may operate according to one or more communication protocols, such as LTE, CDMA, WiMax, WiFi, Bluetooth, HTTP, TCP, and the like. Although the communication network 104 is shown as a single network, it should be understood that the communication network 104 may include multiple, distinct networks that are themselves communicatively linked. The communication network 104 could take other forms as well.

As noted above, the analytics system 106 may be configured to receive data from the assets 102 and the data sources 110. Broadly speaking, the analytics system 106 may include one or more computing systems, such as servers and databases, configured to receive, process, analyze, and output data. The analytics system 106 may be configured according to a given dataflow technology, such as .NET or Nifi, among other examples. The analytics system 106 is discussed in further detail below with reference to FIG. 4.

As shown, the analytics system 106 may be configured to transmit data to the assets 102 and/or to the output systems 108. The particular data transmitted to the assets 102 and/or to the output systems 108 may take various forms and will be described in further detail below.

In general, an output system 108 may take the form of a computing system or device configured to receive data and provide some form of output. The output system 108 may take various forms. In one example, one or more of the output systems 108 may be or include an output device configured to receive data and provide an audible, visual, and/or tactile output in response to the data. In general, an output device may include one or more input interfaces configured to receive user input, and the output device may be configured to transmit data through the communication network 104 based on such user input. Examples of output devices include tablets, smartphones, laptop computers, other mobile computing devices, desktop computers, smart TVs, and the like.

Another example of an output system 108 may take the form of a work-order system configured to output a request for a mechanic or the like to repair an asset. Yet another example of an output system 108 may take the form of a parts-ordering system configured to place an order for a part of an asset and output a receipt thereof. Numerous other output systems are also possible.

The one or more data sources 110 may be configured to communicate with the analytics system 106. In general, a data source 110 may be or include one or more computing systems configured to collect, store, and/or provide to other systems, such as the analytics system 106, data that may be relevant to the functions performed by the analytics system 106. The data source 110 may be configured to generate and/or obtain data independently from the assets 102. As such, the data provided by the data sources 110 may be referred to herein as "external data." The data source 110 may be configured to provide current and/or historical data. In practice, the analytics system 106 may receive data from a data source 110 by "subscribing" to a service provided by the data source. However, the analytics system 106 may receive data from a data source 110 in other manners as well.

Examples of data sources 110 include environment data sources, asset-management data sources, and other data sources. In general, environment data sources provide data indicating some characteristic of the environment in which assets are operated. Examples of environment data sources include weather-data servers, global navigation satellite systems (GNSS) servers, map-data servers, and topography-data servers that provide information regarding natural and artificial features of a given area, among other examples.

In general, asset-management data sources provide data indicating events or statuses of entities that may affect the operation or maintenance of assets (e.g., when and where an asset may operate or receive maintenance). Examples of asset-management data sources include traffic-data servers that provide information regarding air, water, and/or ground traffic, asset-schedule servers that provide information regarding expected routes and/or locations of assets on particular dates and/or at particular times, defect detector systems (also known as "hotbox" detectors) that provide information regarding one or more operating conditions of an asset that passes in proximity to the defect detector system, part-supplier servers that provide information regarding parts that particular suppliers have in stock and prices thereof, and repair-shop servers that provide information regarding repair shop capacity and the like, among other examples.

Examples of other data sources include power-grid servers that provide information regarding electricity consumption and external databases that store historical operating data for assets, among other examples. One of ordinary skill in the art will appreciate that these are but a few examples of data sources and that numerous others are possible.

It should be understood that the network configuration 100 is one example of a network in which embodiments described herein may be implemented. Numerous other arrangements are possible and contemplated herein. For instance, other network configurations may include additional components not pictured and/or more or less of the pictured components.

II. Example Asset

Figure 2:
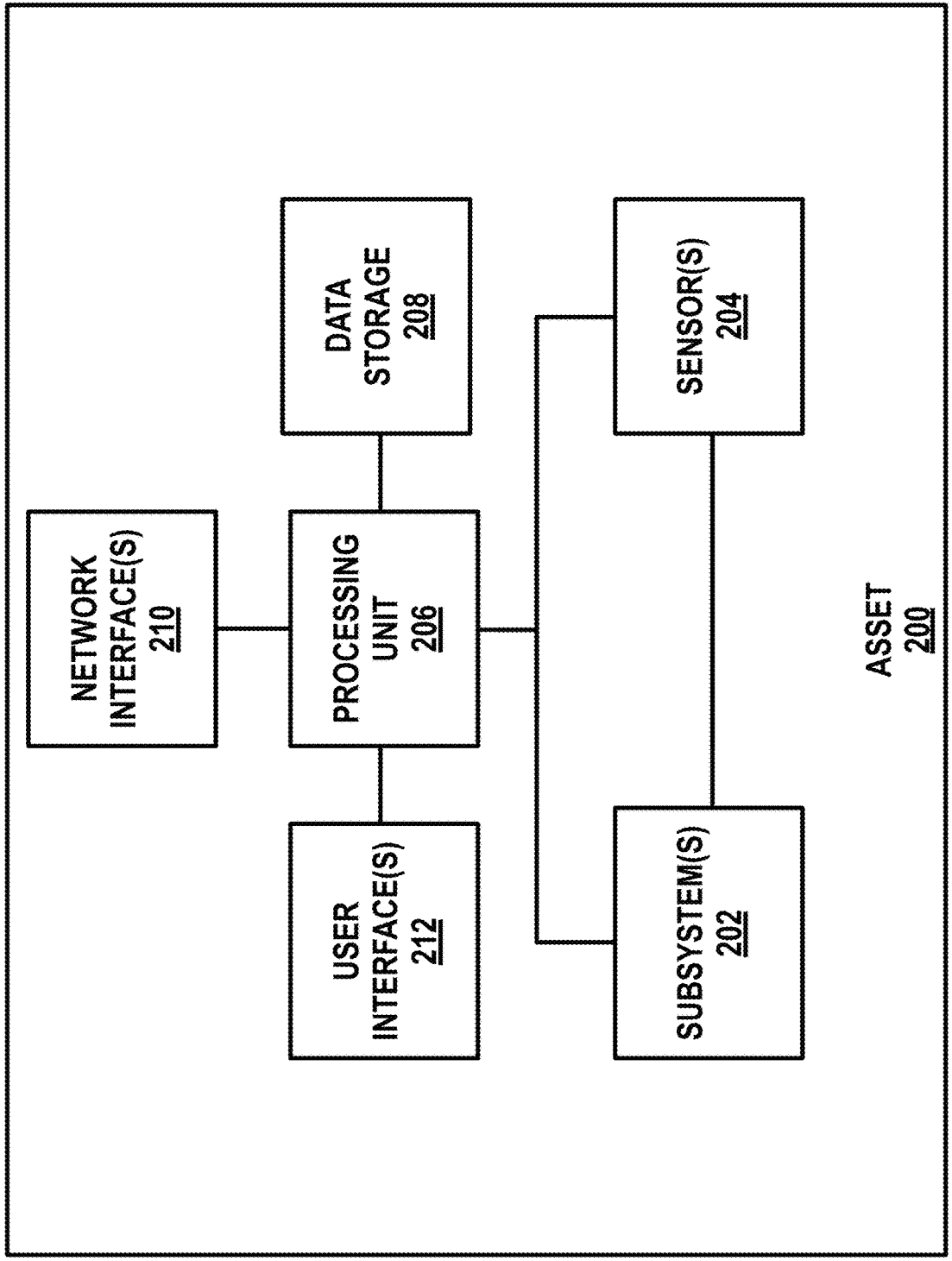
FIG. 2 depicts a simplified block diagram of an example asset.

Turning to FIG. 2, a simplified block diagram of an example asset 200 is depicted. The asset 200 may be one of the assets 102 from FIG. 1. As shown, the asset 200 may include one or more subsystems 202, one or more sensors 204, a processing unit 206, data storage 208, one or more network interfaces 210, and one or more user interfaces 212, all of which may be communicatively linked by a system bus, network, or other connection mechanism. One of ordinary skill in the art will appreciate that the asset 200 may include additional components not shown and/or more or less of the depicted components.

Broadly speaking, the asset 200 may include one or more electrical, mechanical, and/or electromechanical components configured to perform one or more operations. In some cases, one or more components may be grouped into a given subsystem 202.

Generally, a subsystem 202 may include a group of related components that are part of the asset 200. A single subsystem 202 may independently perform one or more operations or the single subsystem 202 may operate along with one or more other subsystems to perform one or more operations. Typically, different types of assets, and even different classes of the same type of assets, may include different subsystems. For instance, in the context of transportation assets, examples of subsystems 202 may include engines, transmissions, drivetrains, fuel systems, battery systems, exhaust systems, braking systems, electrical systems, signal processing systems, generators, gear boxes, rotors, and hydraulic systems, among numerous other examples.

As suggested above, the asset 200 may be outfitted with various sensors 204 that are configured to monitor operating conditions of the asset 200. In some cases, some of the sensors 204 may be grouped based on a particular subsystem 202. In this way, the group of sensors 204 may be configured to monitor operating conditions of the particular subsystem 202.

In general, a sensor 204 may be configured to detect a physical property, which may be indicative of one or more operating conditions of the asset 200, and provide an indication, such as an electrical signal, of the detected physical property. In operation, the sensors 204 may be configured to obtain measurements continuously, periodically (e.g., based on a sampling frequency), and/or in response to some triggering event. In some examples, the sensors 204 may be preconfigured with operating parameters for performing measurements and/or may perform measurements in accordance with operating parameters provided by the processing unit 206 (e.g., sampling signals that instruct the sensors 204 to obtain measurements). In examples, different sensors 204 may have different operating parameters (e.g., some sensors may sample based on a first frequency, while other sensors sample based on a second, different frequency). In any event, the sensors 204 may be configured to transmit electrical signals indicative of a measured physical property to the processing unit 206. The sensors 204 may continuously or periodically provide such signals to the processing unit 206.

For instance, sensors 204 may be configured to measure physical properties such as the location and/or movement of the asset 200, in which case the sensors may take the form of GNSS sensors, dead-reckoning-based sensors, accelerometers, gyroscopes, pedometers, magnetometers, or the like.

Additionally, various sensors 204 may be configured to measure other operating conditions of the asset 200, examples of which may include temperatures, pressures, speeds, friction, power usages, fuel usages, fluid levels, runtimes, voltages and currents, magnetic fields, electric fields, and power generation, among other examples. One of ordinary skill in the art will appreciate that these are but a few example operating conditions that sensors may be configured to measure. Additional or fewer sensors may be used depending on the industrial application or specific asset.

The processing unit 206 may include one or more processors, which may take the form of a general- or special-purpose processor. Examples of processors may include microprocessors, application-specific integrated circuits, digital signal processors, and the like. In turn, the data storage 208 may be or include one or more non-transitory computer-readable storage media, such as optical, magnetic, organic, or flash memory, among other examples.

The processing unit 206 may be configured to store, access, and execute computer-readable program instructions stored in the data storage 208 to perform the operations of an asset described herein. For instance, as suggested above, the processing unit 206 may be configured to receive respective sensor signals from the sensors 204. The processing unit 206 may be configured to store sensor data in and later access it from the data storage 208.

The processing unit 206 may also be configured to determine whether received sensor signals trigger any abnormal-condition indicators, such as fault codes. For instance, the processing unit 206 may be configured to store in the data storage 208 abnormal-condition rules (e.g., fault-code rules), each of which include a given abnormal-condition indicator representing a particular abnormal condition and respective sensor criteria that trigger the abnormal-condition indicator. That is, each abnormal-condition indicator corresponds with one or more sensor measurement values that must be satisfied before the abnormal-condition indicator is triggered. In practice, the asset 200 may be pre-programmed with the abnormal-condition rules and/or may receive new abnormal-condition rules or updates to existing rules from a computing system, such as the analytics system 106.

In any event, the processing unit 206 may be configured to determine whether received sensor signals trigger any abnormal-condition indicators. That is, the processing unit 206 may determine whether received sensor signals satisfy any sensor criteria. When such a determination is affirmative, the processing unit 206 may generate abnormal-condition data and may also cause the asset's user interface 212 to output an indication of the abnormal condition, such as a visual and/or audible alert. Additionally, the processing unit 206 may log the occurrence of the abnormal-condition indicator in the data storage 208, perhaps with a timestamp.

Figure 3:
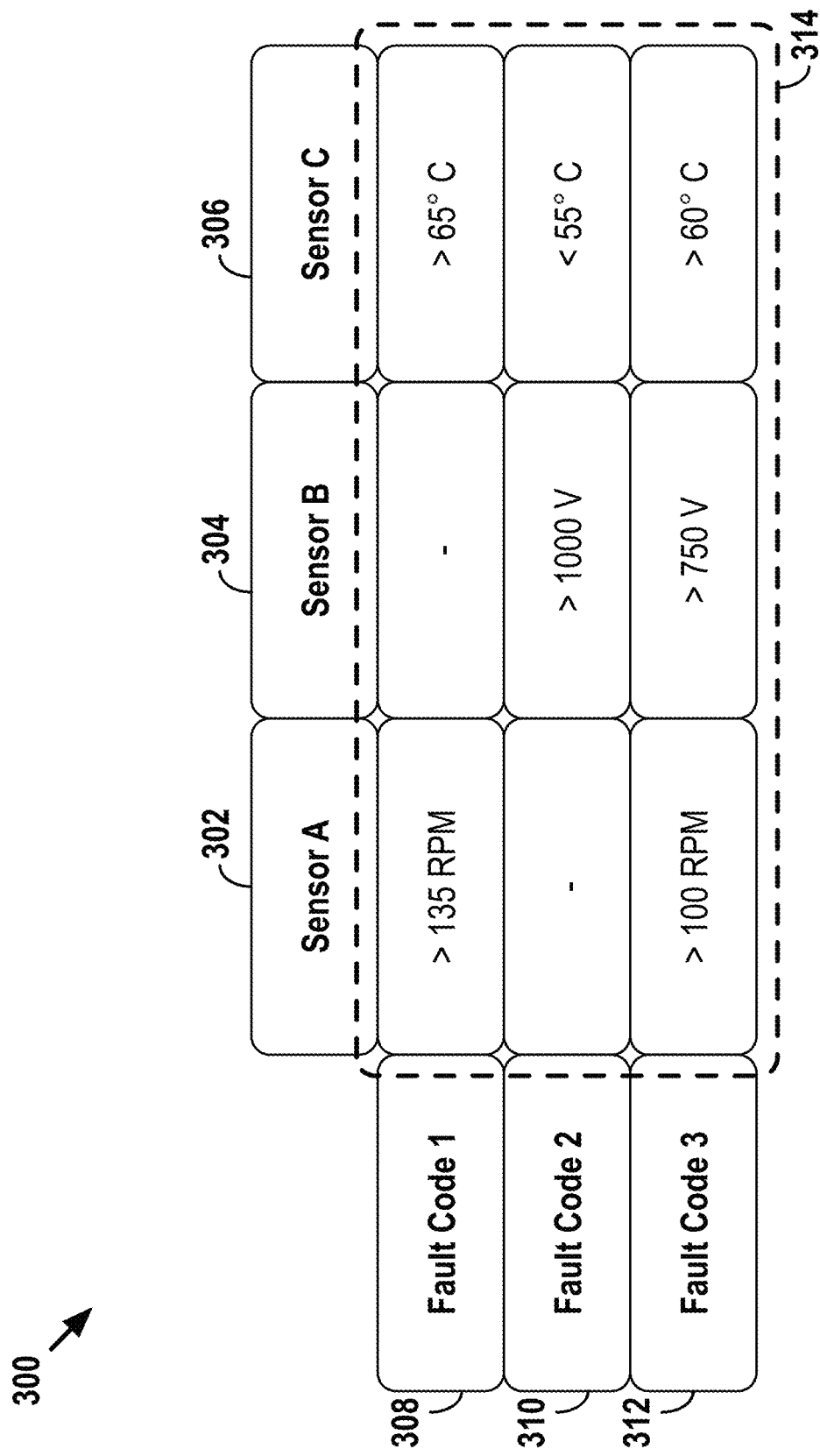
FIG. 3 depicts a conceptual illustration of example abnormal-condition indicators and sensor criteria.

FIG. 3 depicts a conceptual illustration of example abnormal-condition indicators and respective sensor criteria for an asset. In particular, FIG. 3 depicts a conceptual illustration of example fault codes. As shown, table 300 includes columns 302, 304, and 306 that correspond to Sensors A, B, and C, respectively, and rows 308, 310, and 312 that correspond to Fault Codes 1, 2, and 3, respectively. Entries 314 then specify sensor criteria (e.g., sensor value thresholds) that correspond to the given fault codes.

For example, Fault Code 1 will be triggered when Sensor A detects a rotational measurement greater than 135 revolutions per minute (RPM) and Sensor C detects a temperature measurement greater than 65° Celsius (C), Fault Code 2 will be triggered when Sensor B detects a voltage measurement greater than 1000 Volts (V) and a temperature measurement less than 55° C., and Fault Code 3 will be triggered when Sensor A detects a rotational measurement greater than 100 RPM, a voltage measurement greater than 750 V, and a temperature measurement greater than 60° C. One of ordinary skill in the art will appreciate that FIG. 3 is provided for purposes of example and explanation only and that numerous other fault codes and/or sensor criteria are possible and contemplated herein.

Referring back to FIG. 2, the processing unit 206 may be configured to carry out various additional functions for managing and/or controlling operations of the asset 200 as well. For example, the processing unit 206 may be configured to provide instruction signals to the subsystems 202 and/or the sensors 204 that cause the subsystems 202 and/or the sensors 204 to perform some operation, such as modifying a throttle position or a sensor-sampling rate. Moreover, the processing unit 206 may be configured to receive signals from the subsystems 202, the sensors 204, the network interfaces 210, and/or the user interfaces 212 and based on such signals, cause an operation to occur. Other functionalities of the processing unit 206 are discussed below.

The one or more network interfaces 210 may be configured to provide for communication between the asset 200 and various network components connected to communication network 104. For example, at least one network interface 210 may be configured to facilitate wireless communications to and from the communication network 104 and may thus take the form of an antenna structure and associated equipment for transmitting and receiving various over-the-air signals. Other examples are possible as well. In practice, the one or more network interfaces 210 may be configured according to a communication protocol, such as any of those described above.

The one or more user interfaces 212 may be configured to facilitate user interaction with the asset 200 and may also be configured to facilitate causing the asset 200 to perform an operation in response to user interaction. Examples of user interfaces 212 include touch-sensitive interfaces, mechanical interfaces (e.g., levers, buttons, wheels, dials, keyboards, etc.), and other input interfaces (e.g., microphones), among other examples. In some cases, the one or more user interfaces 212 may include or provide connectivity to output components, such as display screens, speakers, headphone jacks, and the like.

One of ordinary skill in the art will appreciate that the asset 200 shown in FIG. 2 is but one example of a simplified representation of an asset and that numerous others are also possible. For instance, in some examples, an asset may include a data acquisition system configured to obtain sensor signals from the sensors where the data acquisition system operates independently from a central controller (such as the processing unit 206) that controls the operations of the asset.

III. Example Analytics System

Referring now to FIG. 4, a simplified block diagram of an example analytics system 400 is depicted. As suggested above, the analytics system 400 may include one or more computing systems communicatively linked and arranged to carry out various operations described herein. Specifically, as shown, the analytics system 400 may include a data intake system 402, a data science system 404, and one or more databases 406. These system components may be communicatively coupled via one or more wireless and/or wired connections.

The data intake system 402 may generally function to receive and process data and output data to the data science system 404. As such, the data intake system 402 may include one or more network interfaces configured to receive data from various network components of the network configuration 100, such as a number of different assets 102 and/or data sources 110. Specifically, the data intake system 402 may be configured to receive analog signals, data streams, and/or network packets, among other examples. As such, the network interfaces may include one or more wired network interfaces, such as a port or the like, and/or wireless network interfaces, similar to those described above. In some examples, the data intake system 402 may be or include components configured according to a given dataflow technology, such as a Nifi receiver or the like.

The data intake system 402 may include one or more processing components configured to perform one or more operations. Example operations may include compression and/or decompression, encryption and/or de-encryption, analog-to-digital and/or digital-to-analog conversion, filtration, and amplification, among other operations. Moreover, the data intake system 402 may be configured to parse, sort, organize, and/or route data based on data type and/or characteristics of the data. In some examples, the data intake system 402 may be configured to format, package, and/or route data based on one or more characteristics or operating parameters of the data science system 404.

In general, the data received by the data intake system 402 may take various forms. For example, the payload of the data may include a single sensor measurement, multiple sensor measurements and/or one or more fault codes. Other examples are also possible.

Moreover, the received data may include certain characteristics, such as a source identifier and a timestamp (e.g., a date and/or time at which the information was obtained). For instance, a unique identifier (e.g., a computer generated alphabetic, numeric, alphanumeric, or the like identifier) may be assigned to each asset, and perhaps to each sensor. Such identifiers may be operable to identify the asset, or sensor, from which data originates. In some cases, another characteristic may include the location (e.g., GPS coordinates) at which the information was obtained. Data characteristics may come in the form of signal signatures or metadata, among other examples.

The data science system 404 may generally function to receive (e.g., from the data intake system 402) and analyze data and based on such analysis, cause one or more operations to occur. As such, the data science system 404 may include one or more network interfaces 408, a processing unit 410, and data storage 412, all of which may be communicatively linked by a system bus, network, or other connection mechanism. In some cases, the data science system 404 may be configured to store and/or access one or more application program interfaces (APIs) that facilitate carrying out some of the functionality disclosed herein.

The network interfaces 408 may be the same or similar to any network interface described above. In practice, the network interfaces 408 may facilitate communication between the data science system 404 and various other entities, such as the data intake system 402, the databases 406, the assets 102, the output systems 108, etc.

The processing unit 410 may include one or more processors, such as any of the processors described above. In turn, the data storage 412 may be or include one or more non-transitory computer-readable storage media, such as any of the examples provided above. The processing unit 410 may be configured to store, access, and execute computer-readable program instructions stored in the data storage 412 to perform the operations of an analytics system described herein.

In general, the processing unit 410 may be configured to perform analytics on data received from the data intake system 402. To that end, the processing unit 410 may be configured to execute one or more modules, which may each take the form of one or more sets of program instructions that are stored in the data storage 412. The modules may be configured to facilitate causing an outcome to occur based on the execution of the respective program instructions. An example outcome from a given module may include outputting data into another module, updating the program instructions of the given module and/or of another module, and outputting data to a network interface 408 for transmission to the assets 102 and/or the output systems 108, among other examples.

The databases 406 may generally function to receive (e.g., from the data science system 404) and store data. As such, each database 406 may include one or more non-transitory computer-readable storage media, such as any of the examples provided above. In practice, the databases 406 may be separate from or integrated with the data storage 412.

The databases 406 may be configured to store numerous types of data, some of which is discussed below. In practice, some of the data stored in the databases 406 may include a timestamp indicating a date and time at which the data was generated or added to the database. Moreover, data may be stored in a number of manners in the databases 406. For instance, data may be stored in time sequence, in a tabular manner, and/or organized based on data source type (e.g., based on asset, asset type, sensor, or sensor type) or fault code, among other examples.

IV. Example Operations

The operations of the example network configuration 100 depicted in FIG. 1 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

The following description may reference examples where a single data source, such as the asset 200, provides data to the analytics system 400 that then performs one or more functions. It should be understood that this is done merely for sake of clarity and explanation and is not meant to be limiting. In practice, the analytics system 400 generally receives data from multiple sources, perhaps simultaneously, and performs operations based on such aggregate received data.

A. Collection of Operating Data

As mentioned above, the representative asset 200 may take various forms and may be configured to perform a number of operations. In a non-limiting example, the asset 200 may take the form of a locomotive that is operable to transfer cargo across the United States. While in transit, the sensors 204 may obtain sensor data that reflects one or more operating conditions of the asset 200. The sensors 204 may transmit the sensor data to the processing unit 206.

The processing unit 206 may be configured to receive sensor data from the sensors 204. In practice, the processing unit 206 may receive sensor data from multiple sensors simultaneously or sequentially. As discussed above, while receiving the sensor data, the processing unit 206 may also be configured to determine whether sensor data satisfies sensor criteria that trigger any abnormal-condition indicators, such as fault codes. In the event the processing unit 206 determines that one or more abnormal-condition indicators are triggered, the processing unit 206 may be configured to perform one or more local operations, such as outputting an indication of the triggered indicator via a user interface 212.

The processing unit 206 may then be configured to transmit operating data for the asset 200 to the analytics system 400 via one of the network interfaces 210 and the communication network 104. For instance, the asset 200 may transmit operating data for to the analytics system 400 continuously, periodically, and/or in response to triggering events (e.g., fault codes). Specifically, the asset 200 may transmit operating data periodically based on a particular frequency (e.g., daily, hourly, every fifteen minutes, once per minute, once per second, etc.), or the asset 200 may be configured to transmit a continuous, real-time feed of operating data. Additionally or alternatively, the asset 200 may be configured to transmit operating data based on certain triggers, such as when sensor measurements from the sensors 204 satisfy sensor criteria for any abnormal-condition indicators. The asset 200 may transmit operating data in other manners as well.

In practice, operating data for the asset 200 may include sensor data and/or abnormal-condition data. In some implementations, the asset 200 may be configured to provide the operating data in a single data stream, while in other implementations the asset 200 may be configured to provide the operating data in multiple, distinct data streams. For example, the asset 200 may provide the analytics system 400 a first data stream of sensor data and a second data stream of abnormal-condition data. Other possibilities also exist.

Sensor data may take various forms. For example, at times, sensor data may include measurements obtained by each of the sensors 204. While at other times, sensor data may include measurements obtained by a subset of the sensors 204.

Specifically, the sensor data may include measurements obtained by the sensors associated with a given triggered abnormal-condition indicator. For example, if a triggered fault code is Fault Code 1 from FIG. 3, then the sensor data may include raw measurements obtained by Sensors A and C. Additionally or alternatively, the sensor data may include measurements obtained by one or more sensors not directly associated with the triggered fault code. Continuing off the last example, the sensor data may additionally include measurements obtained by Sensor B and/or other sensors. In some examples, the processing unit 206 may include particular sensor data in the operating data based on a fault-code rule or instruction provided by the analytics system 400, which may have, for example, determined that there is a correlation between that which Sensor B is measuring and that which caused the Fault Code 1 to be triggered in the first place. Other examples are also possible.

Further still, the sensor data may include one or more sensor measurements from each sensor of interest based on a particular time of interest, which may be selected based on a number of factors. In some examples, the particular time of interest may be based on a sampling rate. In other examples, the particular time of interest may be based on the time at which an abnormal-condition indicator is triggered.

In particular, based on the time at which an abnormal-condition indicator is triggered, the sensor data may include one or more respective sensor measurements from each sensor of interest (e.g., sensors directly and indirectly associated with the triggered fault code). The one or more sensor measurements may be based on a particular number of measurements or particular duration of time around the time of the triggered abnormal-condition indicator.

For example, if the triggered fault code is Fault Code 2 from FIG. 3, the sensors of interest might include Sensors B and C. The one or more sensor measurements may include the most recent respective measurements obtained by Sensors B and C prior to the triggering of the fault code (e.g., triggering measurements) or a respective set of measurements before, after, or about the triggering measurements. For example, a set of five measurements may include the five measurements before or after the triggering measurement (e.g., excluding the triggering measurement), the four measurements before or after the triggering measurement and the triggering measurement, or the two measurements before and the two after as well as the triggering measurement, among other possibilities.

Similar to sensor data, the abnormal-condition data may take various forms. In general, the abnormal-condition data may include or take the form of an indicator that is operable to uniquely identify a particular abnormal condition that occurred at the asset 200 from all other abnormal conditions that may occur at the asset 200. The abnormal-condition indicator may take the form of an alphabetic, numeric, or alphanumeric identifier, among other examples. Moreover, the abnormal-condition indicator may take the form of a string of words that is descriptive of the abnormal condition, such as "Overheated Engine" or "Out of Fuel", among other examples.

The analytics system 400, and in particular, the data intake system 402, may be configured to receive operating data from one or more assets and/or data sources, such as the asset 200. The data intake system 402 may be configured to perform one or more operations to the received data and then relay the data to the data science system 404. In turn, the data science system 404 may analyze the received data and based on such analysis, perform one or more operations.

B. Health Score

As one example, the data science system 404 may be configured to determine a "health score" for an asset, which is a single, aggregated metric that indicates whether a failure will occur at the asset within a given timeframe into the future (e.g., the next two weeks). In particular, in example implementations, a health score may indicate a likelihood that no failures from a group of failures will occur at the asset within a given timeframe into the future, or a health score may indicate a likelihood that at least one failure from a group of failures will occur at the asset within a given timeframe into the future.

In practice, depending on the desired granularity of the health metric, the data science system 404 may also be configured to determine different levels of health metrics. For example, the data science system 404 may determine a health metric for the asset as a whole (i.e., an asset-level health metric). As another example, the data science system 404 may determine a respective health metric for each of one or more subsystems of the asset (i.e., subsystem-level health metrics), which may also then be combined to generate an asset-level health metric. Other examples are also possible.

In general, determining a health metric may involve two phases: (1) a "modeling" phase during which the data science system 404 defines a model for predicting the likelihood of failures occurring and (2) an asset-monitoring phase during which the data science system 404 utilizes the model defined in the machine learning phase and operating data for a given asset to determine a health metric for the given asset.

Figure 5A:
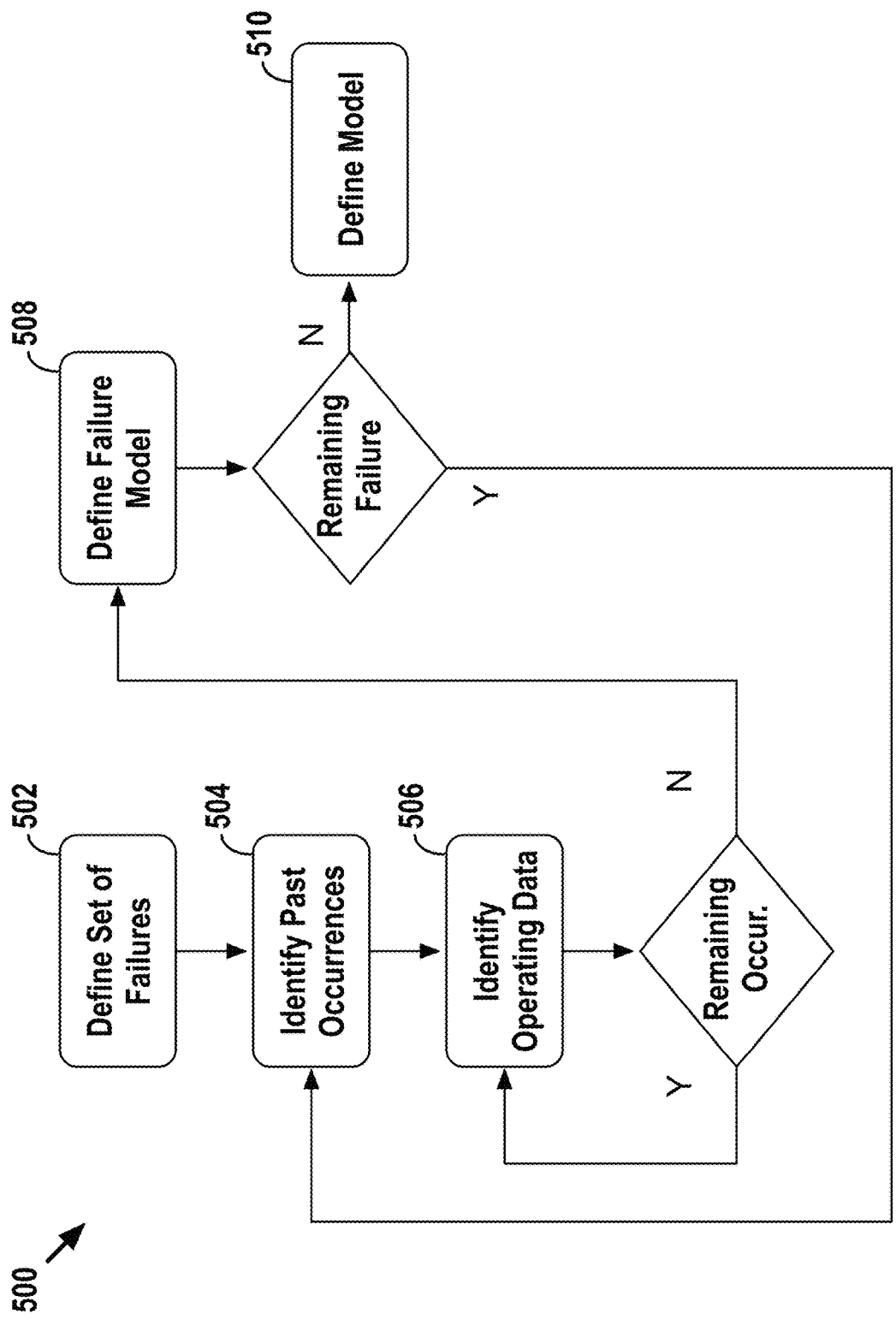
FIG. 5A depicts an example flow diagram of a modeling phase that may be used for determining a health metric.

FIG. 5A is a flow diagram 500 depicting one possible example of a modeling phase that may be used for determining a health metric. For purposes of illustration, the example modeling phase is described as being carried out by the data science system 404, but this modeling phase may be carried out by other systems as well. One of ordinary skill in the art will appreciate that the flow diagram 500 is provided for sake of clarity and explanation and that numerous other combinations of operations may be utilized to determine a health metric.

As shown in FIG. 5A, at block 502, the data science system 404 may begin by defining a set of the one or more failures that form the basis for the health metric (i.e., the failures of interest). In practice, the one or more failures may be those failures that could render an asset (or a subsystem thereof) inoperable if they were to occur. Based on the defined set of failures, the data science system 404 may take steps to define a model for predicting a likelihood of any of the failures occurring within a given timeframe in the future (e.g., the next two weeks).

In particular, at block 504, the data science system 404 may analyze historical operating data for a group of one or more assets to identify past occurrences of a given failure from the set of failures. At block 506, the data science system 404 may identify a respective set of operating data that is associated with each identified past occurrence of the given failure (e.g., sensor data from a given timeframe prior to the occurrence of the given failure). At block 508, the data science system 404 may analyze the identified sets of operating data associated with past occurrences of the given failure to define a relationship (e.g., a failure model) between (1) the values for a given set of operating metrics and (2) the likelihood of the given failure occurring within a given timeframe in the future (e.g., the next two weeks). Lastly, at block 510, the defined relationship for each failure in the defined set (e.g., the individual failure models) may then be combined into a model for predicting the overall likelihood of a failure occurring.

As the data science system 404 continues to receive updated operating data for the group of one or more assets, the data science system 404 may also continue to refine the predictive model for the defined set of one or more failures by repeating steps 504-510 on the updated operating data.

The functions of the example modeling phase illustrated in FIG. 5A will now be described in further detail. Starting with block 502, as noted above, the data science system 404 may begin by defining a set of the one or more failures that form the basis for the health metric. The data science system 404 may perform this function in various manners.

In one example, the set of the one or more failures may be based on one or more user inputs. Specifically, the data science system 404 may receive from a computing system operated by a user, such as an output system 108, input data indicating a user selection of the one or more failures. As such, the set of one or more failures may be user defined.

In other examples, the set of the one or more failures may be based on a determination made by the data science system 404. In particular, the data science system 404 may be configured to define the set of one or more failures, which may occur in a number of manners.

For instance, the data science system 404 may be configured to define the set of failures based on one or more characteristics of the asset 200. That is, certain failures may correspond to certain characteristics, such as asset type, class, etc., of an asset. For example, each type and/or class of asset may have respective failures of interest.

In another instance, the data science system 404 may be configured to define the set of failures based on historical data stored in the databases 406 and/or external data provided by the data sources 110. For example, the data science system 404 may utilize such data to determine which failures result in the longest repair-time and/or which failures are historically followed by additional failures, among other examples.

In yet other examples, the set of one or more failures may be defined based on a combination of user inputs and determinations made by the data science system 404. Other examples are also possible.

At block 504, for each of the failures from the set of failures, the data science system 404 may analyze historical operating data for a group of one or more assets (e.g., fault code data) to identify past occurrences of a given failure. The group of the one or more assets may include a single asset, such as asset 200, or multiple assets of a same or similar type, such as fleet of assets. The data science system 404 may analyze a particular amount of historical operating data, such as a certain amount of time's worth of data (e.g., a month's worth) or a certain number of data-points (e.g., the most recent thousand data-points), among other examples.

In practice, identifying past occurrences of the given failure may involve the data science system 404 identifying the type of operating data, such as abnormal-condition data, that indicates the given failure. In general, a given failure may be associated with one or multiple abnormal-condition indicators, such as fault codes. That is, when the given failure occurs, one or multiple abnormal-condition indicators may be triggered. As such, abnormal-condition indicators may be reflective of an underlying symptom of a given failure.

After identifying the type of operating data that indicates the given failure, the data science system 404 may identify the past occurrences of the given failure in a number of manners. For instance, the data science system 404 may locate, from historical operating data stored in the databases 406, abnormal-condition data corresponding to the indicators associated with the given failure. Each located abnormal-condition data would indicate an occurrence of the given failure. Based on this located abnormal-condition data, the data science system 404 may identify a time at which a past failure occurred.

At block 506, the data science system 404 may identify a respective set of operating data that is associated with each identified past occurrence of the given failure. In particular, the data science system 404 may identify a set of sensor data from a certain timeframe around the time of the given occurrence of the given failure. For example, the set of data may be from a particular timeframe (e.g., two weeks) before, after, or around the given occurrence of the failure. In other cases, the set of data may be identified from a certain number of data-points before, after, or around the given occurrence of the failure.

In example implementations, the set of operating data may include sensor data from some or all of the sensors 204. For example, the set of operating data may include sensor data from sensors associated with a fault code corresponding to the given failure.

Figure 6:
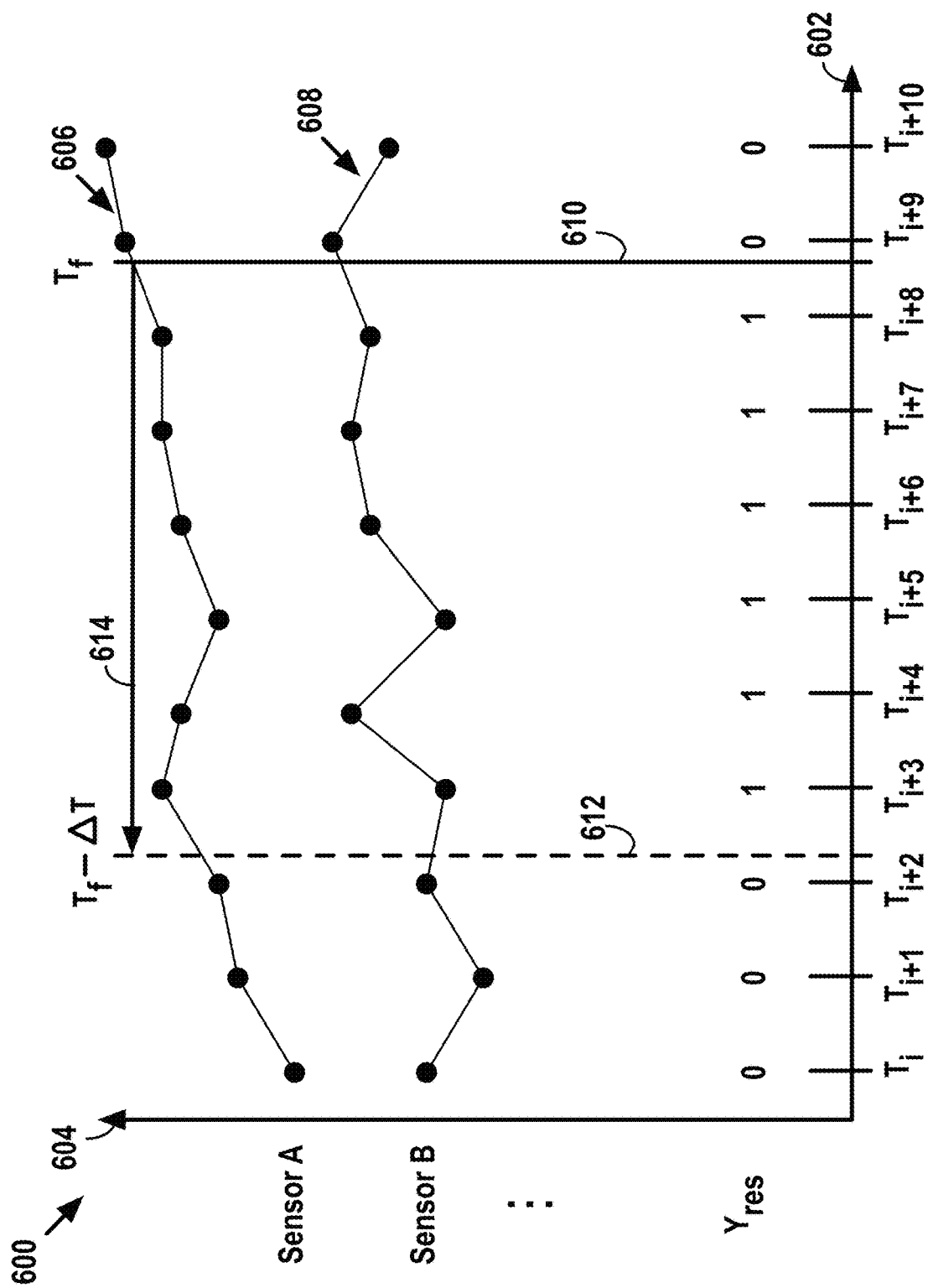
FIG. 6 depicts a conceptual illustration of data utilized to define a model.

To illustrate, FIG. 6 depicts a conceptual illustration of historical operating data that the data science system 404 may analyze to facilitate defining a model. Plot 600 may correspond to a segment of historical sensor data that originated from some (e.g., Sensor A and Sensor B) or all of the sensors 204. As shown, the plot 600 includes time on the x-axis 602, sensor measurement values on the y-axis 604, and sensor data 606 corresponding to Sensor A and sensor data 608 corresponding to Sensor B, each of which includes various data-points representing sensor measurements at particular points in time, $T_i$. Moreover, the plot 600 includes an indication of an occurrence of a failure 610 that occurred at a past time, $T_f$ (e.g., "time of failure"), and an indication of an amount of time 612 before the occurrence of the failure, $\Delta T$, from which sets of operating data are identified. As such, $T_f$–$\Delta T$ defines a timeframe 614 of data-points of interest.

Returning to FIG. 5A, after the data science system 404 identifies the set of operating data for the given occurrence of the given failure (e.g., the occurrence at $T_f$), the data science system 404 may determine whether there are any remaining occurrences for which a set of operating data should be identified. In the event that there is a remaining occurrence, block 506 would be repeated for each remaining occurrence.

Thereafter, at block 508, the data science system 404 may analyze the identified sets of operating data associated with the past occurrences of the given failure to define a relationship (e.g., a failure model) between (1) a given set of operating metrics (e.g., a given set of sensor measurements) and (2) the likelihood of the given failure occurring within a given timeframe in the future (e.g., the next two weeks). That is, a given failure model may take as inputs sensor measurements from one or more sensors and output a probability that the given failure will occur within the given timeframe in the future.

In general, a failure model may define a relationship between operating conditions of the asset 200 and the likelihood of a failure occurring. In some implementations, in addition to raw data signals from sensors 204, a failure model may receive a number of other data inputs, also known as features, which are derived from the sensor signals. Such features may include an average or range of sensor values that were historically measured when a failure occurred, an average or range of sensor-value gradients (e.g., a rate of change in sensor measurements) that were historically measured prior to an occurrence of a failure, a duration of time between failures (e.g., an amount of time or number of data-points between a first occurrence of a failure and a second occurrence of a failure), and/or one or more failure patterns indicating sensor measurement trends around the occurrence of a failure. One of ordinary skill in the art will appreciate that these are but a few example features that can be derived from sensor signals and that numerous other features are possible.

In practice, a failure model may be defined in a number of manners. In example implementations, the data science system 404 may define a failure model by utilizing one or more modeling techniques that return a probability between zero and one, such as a random forest technique, logistic regression technique, or other regression technique.

In a particular example, defining a failure model may involve the data science system 404 generating a response variable based on the historical operating data identified at block 506. Specifically, the data science system 404 may determine an associated response variable for each set of sensor measurements received at a particular point in time. As such, the response variable may take the form of a data set associated with the failure model.

The response variable may indicate whether the given set of sensor measurements is within any of the timeframes determined at block 506. That is, a response variable may reflect whether a given set of sensor data is from a time of interest about the occurrence of a failure. The response variable may be a binary-valued response variable such that if the given set of sensor measurements is within any of determined timeframes, the associated response variable is assigned a value of one, and otherwise, the associated response variable is assigned a value of zero.

Returning to FIG. 6, a conceptual illustration of a response variable vector, $Y_{res}$, is shown on the plot 600. As shown, response variables associated with sets of sensor measurements that are within the timeframe 614 have a value of one (e.g., $Y_{res}$ at times $T_{i+3}$–$T_{i+8}$), while response variables associated with sets of sensor measurements outside the timeframe 614 have a value of zero (e.g., $Y_{res}$ at times $T_i$–$T_{i+2}$ and $T_{+9}$–$T_{i+10}$). Other response variables are also possible.

Continuing in the particular example of defining a failure model based on a response variable, the data science system 404 may train the failure model with the historical operating data identified at block 506 and the generated response variable. Based on this training process, the data science system 404 may then define the failure model that receives as inputs various sensor data and outputs a probability between zero and one that a failure will occur within a period of time equivalent to the timeframe used to generate the response variable.

In some cases, training with the historical operating data identified at block 506 and the generated response variable may result in variable importance statistics for each sensor. A given variable importance statistic may indicate the sensor's relative effect on the probability that a given failure will occur within the period of time into the future.

Additionally or alternatively, the data science system 404 may be configured to define a failure model based on one or more survival analysis techniques, such as a Cox proportional hazard technique. The data science system 404 may utilize a survival analysis technique similarly in some respects to the above-discussed modeling technique, but the data science system 404 may determine a survival time-response variable that indicates an amount of time from the last failure to a next expected event. A next expected event may be either reception of senor measurements or an occurrence of a failure, whichever occurs first. This response variable may include a pair of values that are associated with each of the particular points in time at which sensor measurements are received. The response variable may then be utilized to determine a probability that a failure will occur within the given timeframe in the future.

In some example implementations, a failure model may be defined based in part on external data, such as weather data and/or "hot box" data, among other data. For instance, based on such data, the failure model may increase or decrease an output failure probability.

In practice, external data may be observed at points in time that do not coincide with times at which the sensors 204 obtain measurements. For example, the times at which "hot box" data is collected (e.g., times at which a locomotive passes along a section of railroad track that is outfitted with hot box sensors) may be in disagreement with sensor measurement times. In such cases, the data science system 404 may be configured to perform one or more operations to determine external data observations that would have been observed at times that correspond to the sensor measurement times.

Specifically, the data science system 404 may utilize the times of the external data observations and times of the sensor measurements to interpolate the external data observations to produce external data values for times corresponding to the sensor measurement times. Interpolation of the external data may allow external data observations or features derived therefrom to be included as inputs into the failure model. In practice, various techniques may be used to interpolate the external data with the sensor data, such as nearest-neighbor interpolation, linear interpolation, polynomial interpolation, and spline interpolation, among other examples.

Returning to FIG. 5A, after the data science system 404 determines a failure model for a given failure from the set of failures defined at block 502, the data science system 404 may determine whether there are any remaining failures for which a failure model should be determined. In the event that there remains a failure for which a failure model should be determined, the data science system 404 may repeat the loop of blocks 504-508. In some implementations, the data science system 404 may determine a single failure model that encompasses all of the failures defined at block 502. In other implementations, the data science system 404 may determine a failure model for each subsystem of an asset, which may then be utilized to determine an asset-level failure model (see below for further discussion). Other examples are also possible.

Lastly, at block 510, the defined relationship for each failure in the defined set (e.g., the individual failure models) may then be combined into the model (e.g., the health-metric model) for predicting the overall likelihood of a failure occurring within the given timeframe in the future (e.g., the next two weeks). That is, the model receives as inputs sensor measurements from one or more sensors and outputs a single probability that at least one failure from the set of failures will occur within the given timeframe in the future.

The data science system 404 may define the health-metric model in a number of manners, which may depend on the desired granularity of the health metric. That is, in instances where there are multiple failure models, the outcomes of the failure models may be utilized in a number of manners to obtain the output of the health-metric model. For example, the data science system 404 may determine a maximum, median, or average from the multiple failure models and utilize that determined value as the output of the health-metric model.

In other examples, determining the health-metric model may involve the data science system 404 attributing a weight to individual probabilities output by the individual failure models. For instance, each failure from the set of failures may be considered equally undesirable, and so each probability may likewise be weighted the same in determining the health-metric model. In other instances, some failures may be considered more undesirable than others (e.g., more catastrophic or require longer repair time, etc.), and so those corresponding probabilities may be weighted more than others.

In yet other examples, determining the health-metric model may involve the data science system 404 utilizing one or more modeling techniques, such as a regression technique. In particular, the data science system 404 may regress on the probabilities output by the individual failure models and an aggregate response variable. An aggregate response variable may take the form of the logical disjunction (logical OR) of the response variables (e.g., $Y_{res}$ in FIG. 6) from each of the individual failure models. For example, aggregate response variables associated with any set of sensor measurements that occur within any timeframe determined at block 506 (e.g., the timeframe 614 of FIG. 6) may have a value of one, while aggregate response variables associated with sets of sensor measurements that occur outside any of the timeframes may have a value of zero. Other manners of defining the health-metric model are also possible.

In some implementations, block 510 may be unnecessary. For example, as discussed above, the data science system 404 may determine a single failure model, in which case the health-metric model may be the single failure model.

In practice, the data science system 404 may be configured to update the individual failure models and/or the overall health-metric model. The data science system 404 may update a model daily, weekly, monthly, etc. and may do so based on a new portion of historical operating data from the asset 200 or from other assets (e.g., from other assets in the same fleet as the asset 200). Other examples are also possible.

Figure 5B:
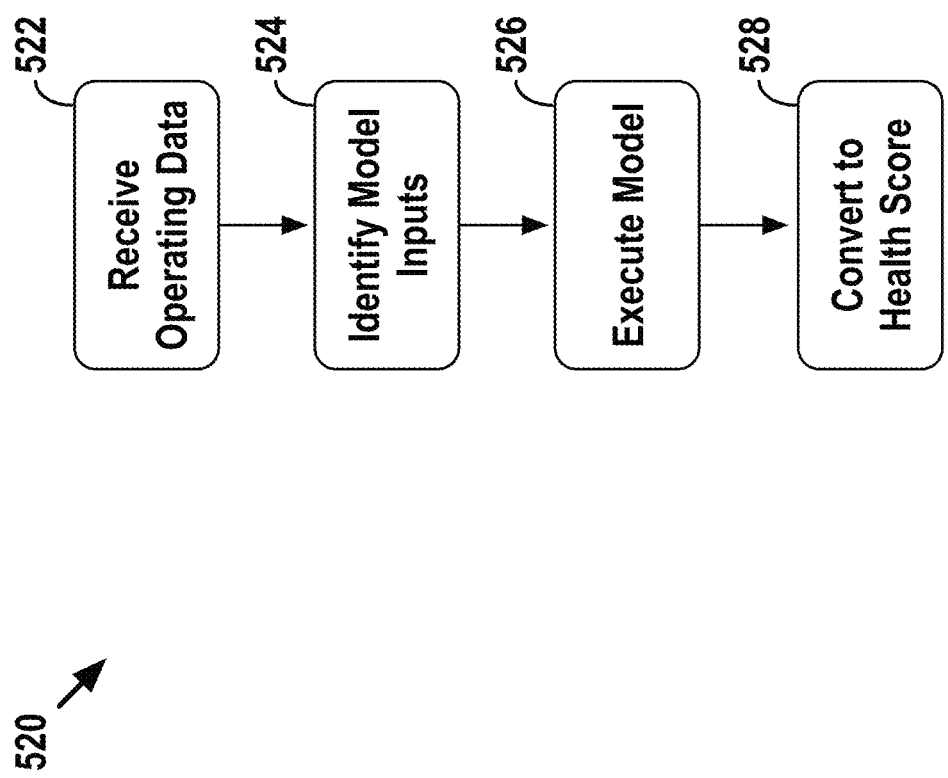
FIG. 5B depicts an example flow diagram of an asset-monitoring phase that may be used for determining a health score.

FIG. 5B is next a flow diagram 520 depicting one possible example of an asset-monitoring phase that may be used for determining a health metric. For purposes of illustration, the example asset-monitoring phase is described as being carried out by the data science system 404, but this asset-monitoring phase may be carried out by other systems as well. One of ordinary skill in the art will appreciate that the flow diagram 520 is provided for sake of clarity and explanation and that numerous other combinations of operations and functions may be utilized to determine a health metric.

As shown in FIG. 5B, at block 522, the data science system 404 may receive data that reflects the current operating conditions of a given asset. At block 524, the data science system 404 may identify, from the received data, the set of operating data that is to be input into the model defined during the modeling phase. At block 526, the data science system 404 may then input the identified set of operating data into the model, which in turn determines and outputs an overall likelihood of a failure occurring within the given timeframe in the future (e.g., the next two weeks). Lastly, at block 528, the data science system 404 may convert this likelihood into the health metric.

As the data science system 404 continues to receive updated operating data for the given asset, the data science system 404 may also continue to update the health metric for the given asset by repeating the operations of blocks 522-528 based on the updated operating data. In some cases, the operations of blocks 522-528 may be repeated each time the data science system 404 receives new data or periodically (e.g., daily, weekly, monthly, etc.). In this way, the analytics system 400 may be configured to dynamically update health metrics, perhaps in real-time, as assets are used in operation.

The functions of the example "asset-monitoring" phase illustrated in FIG. 5B will now be described in further detail. At block 522, the data science system 404 may receive data that reflects the current operating conditions of a given asset. In particular, the data intake system 402 may receive operating data for the asset 200, which is then passed to the data science system 404. In example implementations, the operating data may include at least sensor data from one or more of the sensors 204 but no abnormal-condition data. In other implementations, the operating data may include both. In some examples, the data science system 404 may also receive from data sources 110 external data associated with the present operation of the asset 200.

At block 524, the data science system 404 may identify, from the received data, the set of operating data that is to be input into the health-metric model defined during the modeling phase. This operation may be performed in a number of manners.

In one example, the data science system 404 may identify the set of operating data inputs (e.g., sensor data from particular sensors of interest) for the model based on a characteristic of the given asset, such as asset type or asset class, for which the health metric is being determined. In some cases, the identified set of operating data inputs may be sensor data from some or all of the sensors of the given asset.

In another example, the data science system 404 may identify the set of operating data inputs for the model based on the defined set of failures from block 502 of FIG. 5A. Specifically, the data science system 404 may identify all the abnormal-condition indicators that are associated with the failures from the set of failures. For each of these identified indicators, the data science system 404 may identify the sensors associated with a given indicator. The data science system 404 may set the operating data inputs to include sensor data from each of the identified sensors. Other examples of identifying the set of operating data inputs are also possible.

At block 526, the data science system 404 may then execute the health-metric model. Specifically, the data science system 404 may input the identified set of operating data into the model, which in turn determines and outputs an overall likelihood of at least one failure occurring within the given timeframe in the future (e.g., the next two weeks).

In some implementations, this operation may involve the data science system 404 inputting particular operating data (e.g., sensor data) into the one or more failure models defined at block 508 of FIG. 5A, which each may output an individual probability. The data science system 404 may then use these individual probabilities, perhaps weighting some more than others in accordance with the health-metric model, to determine the overall likelihood of a failure occurring within the given timeframe in the future.

Lastly, at block 528, the data science system 404 may convert the probability of a failure occurring into the health score that may take the form of a single, aggregated parameter that reflects the likelihood that no failures will occur at the asset within the give timeframe in the future (e.g., two weeks). In example implementations, converting the failure probability into the health metric may involve the data science system 404 determining the complement of the failure probability. Specifically, the overall failure probability may take the form of a value ranging from zero to one; the health metric may be determined by subtracting one by that number. Other examples of converting the failure probability into the health metric are also possible.

C. Output of Asset Information

In another aspect, the analytics system 400 may further be configured to facilitate causing one or more of the output systems 108 to output various information regarding an asset in operation, such as an indication of the health metric and perhaps an indication of fault codes and/or sensor data as well. These indications may take various forms.

Figure 7:
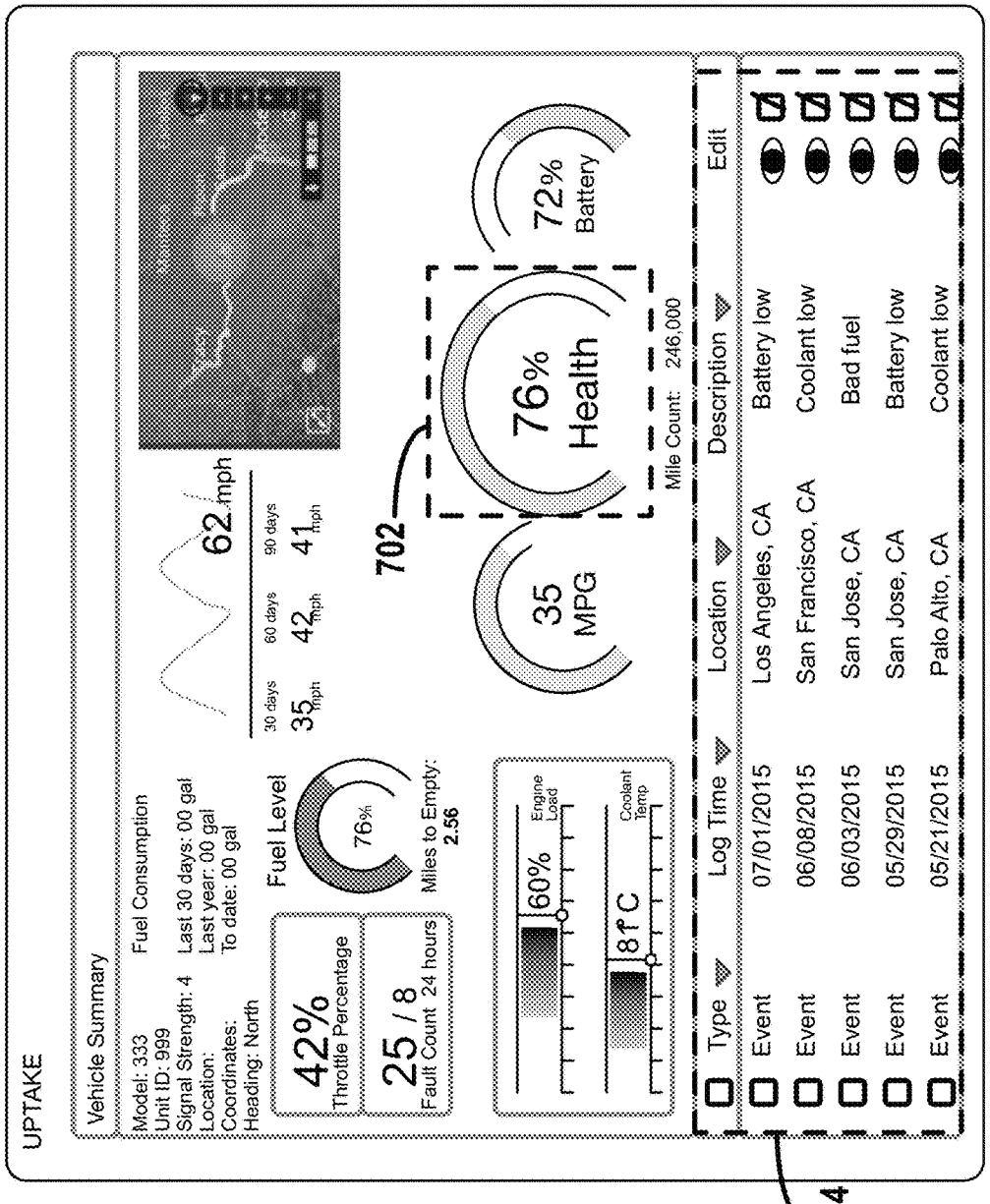
FIG. 7 depicts an example graphical user interface screen showing a representation of a health score.

FIG. 7 depicts an example graphical user interface (GUI) screen 700 that may be displayed by an output system 108 in accordance with instructions from the analytics system 400. This GUI screen 700 is shown to include various information about a given asset (e.g., a vehicle asset). For example, as shown, the GUI screen 700 may include a health-metric display 702 that shows the asset's overall health metric (outlined by the dashed, white box). Here, the health-metric display 702 takes the form of a percentage and a dial-like visualization, but this display may take various other forms as well.

Further, as shown, the GUI screen 700 may include an event log 704 that shows information related to abnormal-condition indicators triggered at the given asset. This event log 704 may include various information regarding the indicators, such as the time that a given indicator was triggered, the location of the asset when the indicator was triggered, and a brief description associated with the indicator. The event log 704 may also include a selectable element for each indicator that, once selected, may cause the graphical user interface 700 to display an indication of the sensor data that contributed to triggering the abnormal-condition indicator. Moreover, as shown, the GUI screen 700 may include other information related to the given asset, such as the asset's current location and various key performance indicators. Various other example GUI screens are possible as well.

D. Triggering Actions Based on Health Score

As another aspect, the analytics system 400 may be configured to use a health metric to trigger one or more actions that may help modify the health metric of the asset 200. In some cases, if the health metric falls below a particular threshold value, an action may be triggered that may facilitate increasing the health metric of the asset 200. Such actions may be referred to herein as "preventative actions" in that these actions aim to help prevent a failure from occurring.

In particular, the data science system 404 may be configured to monitor the health metric generated for the asset 200 and determine whether the health metric reaches a threshold value, which may have been predetermined and stored in a database 406 or dynamically determined by the data science system 404. Various actions are possible in the event that the health metric does fall below the threshold.

For example, the analytics system 400 may be configured to cause an output system 108 to display a warning or alert. For instance, the warning or alert may include a visual, audible, or combination thereof indication of the decreasing health metric. In a particular case, the analytics system 400 may case the output system 108 to display animated visualizations, such as flashing or growing visualizations, and/or output an alarm sound or the like.

In another example, based on the health metric reaching a threshold value, the analytics system 400 may generate a list of one or more recommended actions that may help increase the health metric. For instance, a recommended action may be to repair a particular subsystem of the asset 200, to operate the asset 200 according to certain operating conditions, or to steer the asset 200 around a particular geographical region, among other examples. The analytics system 400 may then cause an output system 108 to output an indication of the recommended actions.

In other examples, based on the health metric reaching a threshold value, the analytics system 400 may be configured to cause a work-order system to generate a work order to repair the asset 200. In particular, the analytics system 400 may transmit work-order data to a work-order system that causes the work-order system to output a work order, which may specify a certain repair that may help increase the health metric. Similarly, the analytics system 400 may be configured to transmit part-order data to cause a parts-ordering system to order a particular part for the asset 200 that may be needed in the repair of the asset 200. Other possibilities also exist.

In yet other examples, based on the health metric reaching a threshold value, the analytics system 400 may be configured to transmit to the asset 200 one or more commands that facilitate modifying one or more operating conditions of the asset 200. For instance, a command may cause the asset 200 to decrease (or increase) velocity, acceleration, fan speed, propeller angle, and/or air intake, among other examples. Other actions are also possible.

E. Recommended Operating Mode

As discussed above, the analytics system 400 may use a health-metric model as a basis for generating one or more indicators related to the asset's operation. In one specific aspect, the analytics system 400 may determine a "recommended operating mode" of an asset, which is a recommendation of a particular manner in which the given asset should be used that may take into account both (1) whether any failure type of a group of failure types is predicted to occur at the asset in the foreseeable future and (2) a categorization of the particular failure type(s) that are predicted to occur in the foreseeable future (e.g., a failure severity level or other type of categorization based on safety, compliance, or the like). In other words, the "recommended operating mode" of an asset may be based not only on whether a failure is predicted to occur at an asset in the foreseeable future, but also on the categorization of the failure that is predicted to occur at the asset—which may help an individual responsible for overseeing the asset make a more informed decision as to how the asset should be used (e.g., whether the manner in which the asset is being used should be changed).

In practice, the recommended operating mode for the given asset may be selected from a predefined set of recommended operating mode options, which may take various forms. As one possible example, a set of recommended operating mode options may include an "Inoperable" (or "Do Not Operate") mode, which represents a recommendation that an asset should not be used due to a prediction of a forthcoming failure that is expected to impact the asset's operation in a critical way, one or more "Limited Use" modes, which each represent a recommendation that an asset should only be used in a limited manner due to a prediction of a forthcoming failure that is expected to impact the asset's operation in some meaningful way (e.g., a "Trail Only" or "Non-Lead" mode for a locomotive), and a "Full Operation" mode, which represents a recommendation that an asset can be used at its full capacity because it is either unlikely to fail or is only likely to fail in a manner that is not expected to impact the asset's operation in a meaningful way. However, the set of recommended operating mode options may take various other forms as well, including the possibility that the recommended operating modes may be customized for particular asset types, particular industries, and/or particular end users, as examples. It should also be understood that a recommended operating mode could potentially include a more detailed recommendation of how to operate an asset than the examples set forth above (e.g., a recommended operating mode may comprise a set of multiple recommendations as to how to operate multiple different subsystems or components of the asset). Likewise, it should be understood that the recommended operating modes may take different forms depending on the particular approach used for categorizing the failure types (e.g., a severity-based categorization vs. a safety-based or compliance-based categorization).

Further, in practice, the predefined set of recommended operating mode options may be established in various manners. As examples, a default set of recommended operating mode options may be preassigned by the analytics system 400 (e.g., based on input from a subject matter expert) and/or the predefined set of recommended operating mode options may be assigned based on user input from an end user (e.g., an owner and/operator of assets), among other possibilities. Further, the predefined set of recommended operating mode options may also be updated at various times, such as periodically according to a schedule and/or in response to a particular triggering event (e.g., a user request to update the recommended operating modes). In this respect, it may be possible for an end user to modify the predefined set of recommended operating mode options (e.g., to override a default set of recommended operating mode options that were preassigned by data analytics system 400 based on input from a subject matter expert or the like), which may allow different end users to customize the recommended operating modes to their own preferences. Further yet, as described in further detail below, the recommended operating mode options may each be associated with a color coding that may be used when an asset's recommended operating mode is surfaced to a user.

Figure 8:
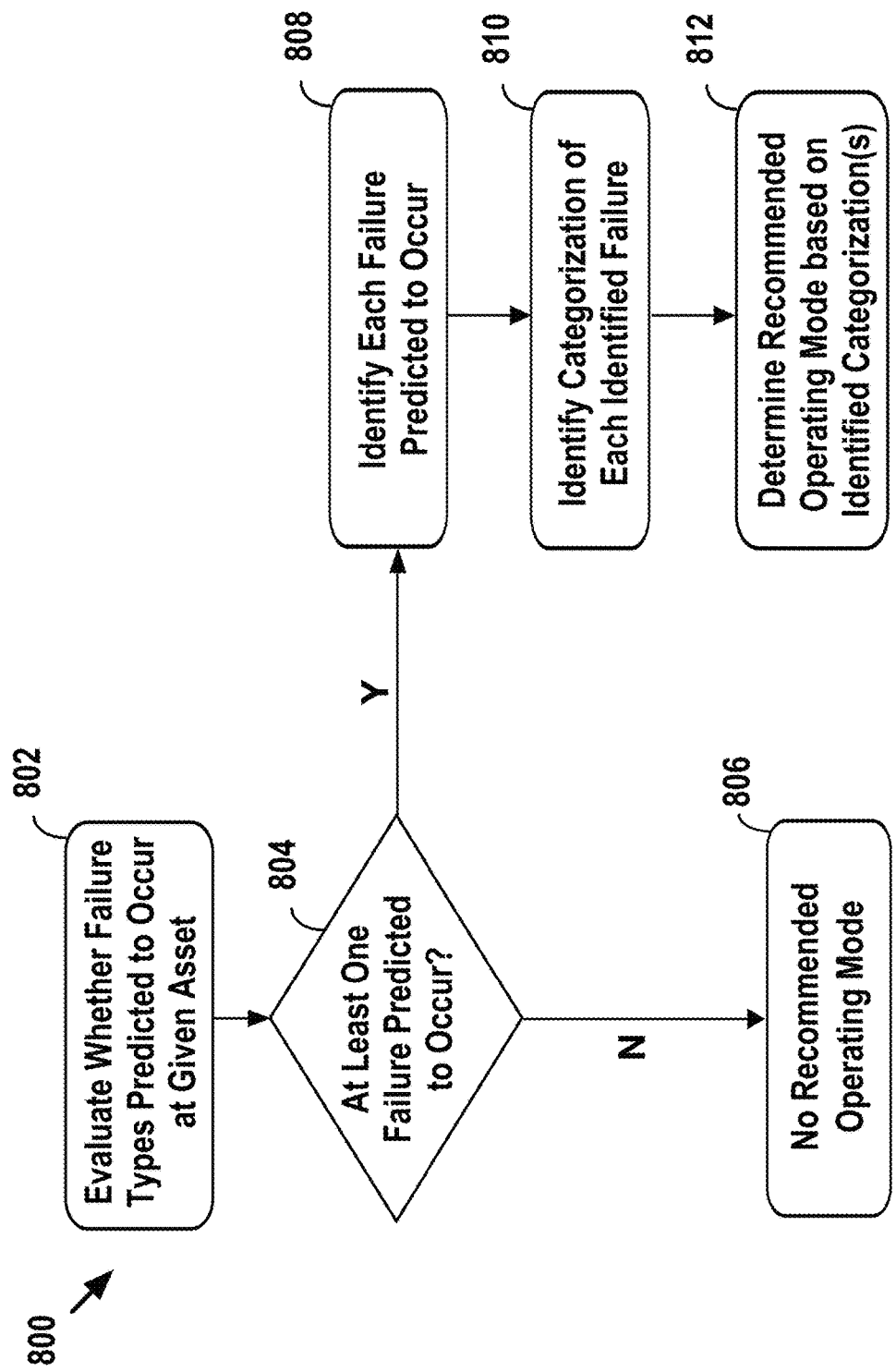
FIG. 8 depicts an example flow diagram of an example process for determining a recommended operating mode of an asset.

The process for determining a recommended operating mode of an asset may take various forms. FIG. 8 is a flow diagram 800 depicting one possible example of a process for determining a recommended operating mode of an asset. For purposes of illustration, the example process is described as being carried out by the analytics system 400, but this process may be carried out by other systems as well. One of ordinary skill in the art will appreciate that the flow diagram 800 is provided for sake of clarity and explanation and that numerous other combinations of operations may be utilized to determine a recommended operating mode of an asset.

At block 802, the analytics system 400 may evaluate whether each failure type of a group of failure types is predicted to occur at a given asset. The analytics system 400 may perform this evaluation in various manners.

In one implementation, the analytics system 400 may perform this evaluation using a health-metric model such as the one described above, which may comprise a collection of multiple individual failure models that are each configured to predict a likelihood of an individual failure type in a group of failure types occurring at the given asset in the foreseeable future (e.g., within the next two weeks). In such an implementation, the analytics system 400 may begin by inputting operating data for the given asset (e.g., sensor data) into the health-metric model, which may cause each individual failure model of the health-metric model to output a respective likelihood value (e.g., a probability) indicating the likelihood of the model's individual failure type occurring at the given asset in the foreseeable future.

In line with the discussion above, the health-metric model may be configured to aggregate these respective likelihood values for the individual failure types in the group into an aggregated health score for the given asset (e.g., by taking the maximum, median, normal average, or weighted average of the respective likelihood values for the individual failure types and then using either the resulting value or the complement thereof as the aggregated health score). However, instead of (or in addition to) using the health-metric model's output of the respective likelihood values for the individual failure types in the group in this manner, the analytics system 400 may use the health-metric model's output of the respective likelihood values for the individual failure types in the group to evaluate whether each individual failure type of the group of failure types is predicted to occur at the given asset.

For instance, after using the health-metric model's collection of individual failure models to determine the respective likelihood values for the individual failure types in the group, the analytics system 400 may (1) compare the respective likelihood value for each individual failure type in the group of failure types to a threshold value that defines whether an individual failure type is predicted to occur at the given asset (e.g., a failure likelihood of 80 or higher) and then (2) identify each individual failure type having a respective likelihood value that exceeds the threshold value as a failure type that is predicted to occur at the given asset in the foreseeable future. In this respect, the analytics system 400 either may use the same threshold value to evaluate each individual failure type or may use different threshold values to evaluate different individual failure types, where each such threshold value may be assigned based on user input (e.g., a subject matter expert, an end user, or the like) and/or based on an analysis of historical data that is carried out by the analytics system 400, among other possibilities.

While the analytics system's evaluation of whether each individual failure type of the group of failure types is predicted to occur at the given asset is described above with reference to a health-metric model that comprises a predefined collection of individual failure models, it should be understood that the analytics system 400 may perform this evaluation using any set of individual failure models related to the operation of an asset, regardless of whether or not the individual failure models are considered to be part of a health-metric model (i.e., regardless of whether or not such individual failure models are part of a predefined collection of individual failure models that are to be used together). For example, the analytics system 400 may be provisioned with a respective individual failure model for each of various different possible failure types that could occur at an asset, and the analytics system 400 may choose which of these individual failure models to use for determining a recommended operating mode of an asset in a dynamic manner based on factors such as the type of asset, the assigned responsibility of the asset at the time of the determination, the location of the asset at the time of the determination, and/or the weather conditions at or near the asset's location at the time of the determination, among other examples.

Further, in practice, the analytics system 400 may perform the evaluation of whether each individual failure type of the group of failure types is predicted to occur at the given asset at various times. As one possibility, the analytics system 400 may be configured to perform this evaluation according to a schedule. As another possibility, the analytics system 400 may be configured to perform this evaluation in response to any of various types of triggering events. For example, the analytics system 400 may be configured to perform this evaluation in response to detecting that new operating data for an asset is available for evaluation. As another example, the analytics system 400 may be configured to perform this evaluation in response to determining that an aggregated health score for an asset satisfies certain threshold criteria indicating that the asset appears to be in a state of impending failure. In this respect, the threshold criteria used to determine whether an asset is considered to be in a state of impending failure could either be the same as the criteria used to determine whether to trigger a preventative action (e.g., one of the preventative actions described above) or different from the criteria used to determine whether to trigger a preventative action. As yet another example, the analytics system 400 may be configured to perform this evaluation in response to receiving a user request (e.g., a request to view an asset's recommended operating mode entered via a client station in communication with the analytics system 400). The analytics system 400 may perform the evaluation of whether each individual failure type of the group of failure types is predicted to occur at the given asset at various other times as well.

As a result of performing the evaluation at block 802 of whether each failure type from the group of failure types is predicted to occur at the given asset, the analytics system 400 may reach one of two determinations at block 804: (1) that no failure type from the group of failure types is predicted to occur at the given asset or (2) that at least one failure type from the group of failure types is predicted to occur at the given asset. The analytics system 400 may then proceed in one of two different manners depending on which one of these determinations is reached.

For instance, if the analytics system 400 determines at block 804 that no failure type from the group of failure types is predicted to occur at the given asset, then as shown at block 806, the analytics system 400 may decide that no recommended operating mode should be assigned to the given asset. In this respect, a decision not to assign a recommended operating mode to assets that are not predicted to experience failures in the foreseeable future may allow a user to more easily differentiate between these assets and other assets that are predicted to experience failures in the foreseeable future and potentially require more of the user's attention, which may improve user experience. However, as an alternative to deciding not to assign a recommended operating mode for the given asset at block 806, the analytics system 400 may choose to assign the most favorable mode from a predefined set of recommended operating mode options to the given asset (e.g., "Fully Operational"). As yet another alternative, the analytics system 400 may assign a special type of recommended operating mode to the given asset that is only available for assets that are not predicted to experience failures in the foreseeable future. The analytics system 400 may decide how to handle the recommended operating mode for an asset that is not predicted to experience any failures in the foreseeable future in other manners as well.

On the other hand, if the analytics system determines at block 804 that that at least one failure type from the group of failure types is predicted to occur at the given asset, then the analytics system 400 may carry out a set of functions to determine a particular recommended operating mode for the given asset. In this respect, each failure type in the group of failure types may be assigned a particular categorization from a set of possible categorization options, which may provide an indication how a failure type may impact the operation of the given asset. This set of possible categorization options may take various forms.

As one possible implementation, the set of possible categorization options may take the form of a set of failure severity levels, which may provide an indication of how severely an asset's operation is expected to be impacted by an occurrence of the failure type (i.e., how critical the failure type is expected to be). For example, the set of failure severity levels may include one or more "high" (or "critical") severity levels used to indicate failure types that are expected to have a significant impact on an asset's operation (e.g., a failure type that is expected to render an asset inoperable), one or more "medium" severity levels used to indicate failure types that are expected to have a moderate impact on an asset's operation (e.g., a failure type that is expected to limit an asset's operation but not render it inoperable), and/or one or more "low" severity levels used to indicate failure types that are expected to have minimal impact on an asset's operation, among other possibilities. Further, the manner in which the set of failure severity levels is represented may take various forms, examples of which include a set of textual indicators (e.g., "High," "Medium," "Low," etc.), a scale of numerical indicators, or the like. The set of failure severity levels may include other types of levels and/or take various other forms as well.

It is also possible that set of possible categorization options for the failure types may take other forms as well. For example, the set of possible categorization options may include a set of categorization options based on safety or compliance in a particular industry, among other examples.

Further, the categorizations of the failure types may be assigned in various manners. As examples, the failure types' categorizations may be preassigned by the analytics system 400 (e.g., based on input from a subject matter expert and/or analysis of historical data) and/or may be assigned based on user input from an end user (e.g., an owner/operator of assets), among other possibilities. Further yet, the failures types' categorization assignments may be updated at various times, such as periodically according to a schedule and/or in response to a particular triggering event (e.g., a user request to update the categorization assignments for certain failures type and/or a detection of a new failure type that needs to be assigned a categorization). In this respect, it may be possible for a user to modify the categorizations that are assigned to the failure types in the group (e.g., to override a categorization that was preassigned by data analytics system 400 with a categorization that is more or less severe), which may allow users to tailor the categorizations of the failure types to their respective preferences for approaching failures.

In some implementations, it is also possible that the analytics system 400 may maintain different sets of categorization assignments for different users. For example, the analytics system 400 may be configured to maintain and use a first set of categorization assignments for a user responsible for asset maintenance and a second set of categorization assignments for a user responsible for asset operations.

Further, in some implementations, it is also possible that the categorization assignments of the failure types may vary depending on factors such as asset type, asset responsibilities, asset location, weather conditions at or near the asset, etc. For example, the analytics system 400 may be configured to maintain and use a first set of categorization assignments for a first set of asset responsibilities, a second set of categorization assignments for a second set of asset responsibilities, and so on. Many other examples are possible as well.

The categorization assignments for the group of failure types may take various other forms and be established in various other manners as well.

Once the categorization assignments for the group of failure types are established, the analytics system 400 may then use these categorization assignments to determine the recommended operating mode of the given asset at times when at least one failure type from the group of failure types is predicted to occur at the given asset.

For instance, if the analytics system 400 determines at block 804 that that at least one failure type from the group of failure types is predicted to occur at the given asset, then the analytics system 400 may first proceed to block 808, where the analytics system 400 may identify each particular failure type from the group of failure types that is predicted to occur at the given asset. In this respect, the analytics system 400 may make this identification based on the evaluation performed at block 802 (e.g., by identifying each failure type having a likelihood value that exceeds a threshold value). However, the analytics system 400 may identify each particular failure type that is predicted to occur at the given asset in other manners as well.

In turn, at block 810, the analytics system 400 may determine a respective categorization (e.g., severity level, safety level, compliance level, etc.) of each identified failure type. The analytics system 400 may carry out this function in various manners.

In one implementation, the analytics system 400 may maintain and/or have access to data that specifies the current categorization assigned to each failure type in the group of failure types, in which case the analytics system 400 may use this data to determine the categorization of each identified failure type. In another implementation, the individual failure models discussed above may each be configured to output the particular categorization assigned to the model's respective failure type along with the likelihood of the respective failure type occurring at an asset, in which case the analytics system 400 may use the categorization output by each individual failure model that predicted an identified failure type to determine the categorization of each identified failure type. The analytics system 400 may determine the categorization of each identified failure type in other manners as well.

In line with the discussion above, in some implementations, the determination of a respective categorization of each identified failure type may also be based on factors such as asset type, asset responsibilities, asset location, and/or weather conditions at or near the asset, among other possibilities. For example, if the given asset is a locomotive and the analytics system 400 has predicted the occurrence of a throttle failure that precludes the locomotive from getting up to full throttle, such a failure type may have a lower severity level if the locomotive's current responsibility is to assemble trains and a higher severity level if the locomotive's current responsibility is to haul freight across the country. Many other examples are possible as well.

Lastly, at block 812, the analytics system 400 may use the determined categorization of each identified failure type that is predicted to occur at the given asset as a basis for determining the recommended operating mode of the given asset. The analytics system 400 may carry out this function in various manners.

In one implementation, the analytics system 400 may begin by selecting a representative categorization for the identified one or more failure types that are predicted to occur at the given asset. The analytics system 400 may make this selection in various manners.

As one possibility, if the analytics system 400 has identified only one failure type that is predicted to occur, then the categorization of that one identified failure will preferably be selected as the representative categorization. On the other hand, if the analytics system 400 has identified multiple different failure types that are predicted to occur at the given asset and these identified failure types have different categorizations, the analytics system 400 may select one of these categorizations to use as the representative categorization. In this respect, the analytics system 400 may use various criteria to select between different categorizations assigned to identified failure types. For example, if the categorizations of the identified failure types take the form of severity levels, then the analytics system 400 may select the highest of the severity levels assigned to the identified failure types as the representative severity level. However, it should be understood that the representative categorization for the identified one or more failures may be determined in other manners as well.

Based on the foregoing, it should be understood that the recommended operating mode of the given asset may not necessarily be dictated by which failure type is most likely to occur at the given asset. Rather, in a scenario where there are multiple failure types that are likely to occur at the given asset (e.g., multiple failure types having likelihood values that exceed a threshold value), the recommended operating mode of the given asset may be dictated by whichever of these failure types is viewed to have the most significant impact on the given asset's operation (e.g., in terms of severity, safety, compliance, or the like), regardless of whether that failure type is the most likely to occur.

After selecting the representative categorization for the identified one or more failures that are predicted to occur, the analytics system 400 may then identify a recommended operating mode that corresponds to the representative categorization—which is deemed to be the recommended operating mode for the given asset. The analytics system 400 may perform this function in various manners.

As one possibility, the analytics system 400 may maintain and/or otherwise have access to data that defines a correlation between categorization options and recommended operating modes, in which case the analytics system 400 may use the representative categorization in combination with this correlation data to identify the recommended operating mode corresponding to the representative categorization, which is considered to be the recommended operating mode of the given asset. In practice, the data that defines the correlation between categorization options and recommended operating modes may take various forms.

For instance, continuing with the example discussed above where the categorization options comprise set of failure severity levels, the severity levels may be correlated with recommended operating modes as follows:

| Severity Level | Recommended Operating Mode |
| --- | --- |
| High | Do Not Operate |
| Med/high | Limited Use Type #1 |
| Med/low | Limited Use Type #2 |
| Low | Full Operation |

However, it should be understood that this example is merely being provided for purposes of illustration, and that the correlation between categorizations options and recommended operating modes could take numerous other forms as well, including the possibility that there may be more or less categorizations and/or recommended operating modes, that the same recommended operating mode may be correlated with multiple different categorizations options (e.g., there may be a single "Limited Use" operating mode that may be correlated with both "medium" severity levels), and/or that the recommended operating modes may be represented as something other than textual descriptors, among other possibilities.

Further, the correlations between the categorization options and the recommended operating modes may be established in various manners. As examples, these correlations may be preassigned by the analytics system 400 (e.g., based on input from a subject matter expert) and/or may be assigned based on user input from an end user (e.g., an owner and/operator of assets), among other possibilities. Further yet, the correlations between the categorization options and the recommended operating modes may also be updated at various times, such as periodically according to a schedule and/or in response to a particular triggering event (e.g., a user request to update the recommended operating modes). In this respect, it may be possible for an end user to modify the recommended operating mode that is associated with a given categorization option (e.g., to override a default correlation that was preassigned by the analytics system 400 based on input from a subject matter expert or the like).

In some implementations, it is also possible that data analytics system 400 may maintain different correlations between categorization options and the recommended operating modes for different users. For example, the analytics system 400 may be configured to maintain and use a first set of correlations for a user responsible for asset maintenance and a second set of correlations for a user responsible for asset operations. Many other examples are possible as well.

Further, in some implementations, it is possible that the correlations between categorization options and recommended operating modes may vary depending on factors such as asset type, asset responsibilities, asset location, weather conditions at or near the asset, etc. For example, the analytics system 400 may be configured to maintain and use a first set of correlations for a first set of asset responsibilities, a second set of categorization assignments for a second set of asset responsibilities, and so on. Many other examples are possible as well.

While the failure type categorizations and recommended operating modes are described above as separate concepts, it should also be understood that the categorization options for the failure types could be the recommended operating modes themselves. For instance, in one implementation, the categorizations assigned to the failure types may take the form of textual descriptions that also represent recommended operating modes, such that when the representative categorization of the identified one or more failure types is selected, this simultaneously serves as a selection of the recommended operating mode for the given asset. In such an implementation, rather than assigning a severity level, a safety level, a compliance level, etc. to each failure type and then correlating these levels to recommended operating modes, the analytics system 400 may assign recommended operating modes to failure types directly (e.g., a first failure type may be assigned a recommendation of "Do Not Operate," a second failure type may be assigned a recommendation of "Limited Use," etc.). In this respect, as discussed above, the recommended operating modes may also take different forms depending on the particular approach used for categorizing the failure types (e.g., a severity-based categorization vs. a safety-based or compliance-based categorization).

The determined categorization of each identified failure that is predicted to occur at the given asset may be used to determine the recommended operating mode of the given asset in other manners as well.

In line with the discussion above, in some implementations, the analytics system's determination of the recommended operating mode of the given asset may also be based on factors such as asset type, asset responsibilities, asset location, and/or weather conditions at or near the asset, among other possibilities. For instance, continuing with the example above where the given asset is a locomotive and the analytics system 400 has predicted the occurrence of a throttle failure that precludes the locomotive from getting up to full throttle, a more favorable operating mode may be recommended for the locomotive if its current responsibility is to assemble trains (e.g., "Full Operation") and a less favorable operating mode may be recommended for the locomotive if its current responsibility is to haul freight across the country (e.g., "Limited Use"). Many other examples are possible as well.

The analytics system 400 may determine the recommended operating mode of an asset in other manners as well.

Once the given asset's recommended operating mode has been determined, the analytics system 400 may then use the recommended operating mode of the given asset as a basis for carrying out actions that are similar to those described above with respect to the output of a health-metric model.

For instance, as one possibility, the analytics system 400 may facilitate causing one or more of the output systems 108 to display the recommended operating mode of the given asset, either alone or together with the recommended operating modes of various other assets. In this respect, the display of an asset's recommended operating mode may take various different forms, examples of which may include a textual representation of the recommended operating mode (e.g., "Inoperable," "Limited Use," "Fully Operational," etc.) and/or a numerical representation of the recommended operating mode (e.g., a 3 for an "Inoperable" state, a 2 or 1 for a "Limited Use" state, and a 0 for a "Fully Operational" state), among other possibilities.

In some implementations, the assets' recommended operating modes could also be color coded in a manner that enables a user to more quickly identify which assets have recommended operating modes that are of most concern (e.g., assets with an "Inoperable" recommended operating mode) versus which assets have recommended operating modes that are of least concern (e.g., assets with a "Fully Operational" recommended operating mode). As one possible example, an "Inoperable" mode may be displayed in red, an a "Limited Use" mode may be displayed in orange or yellow, and a "Fully Operational" mode may either be displayed in green or have no color at all. Further, as with the recommended operating modes themselves, this color coding may be preassigned by the analytics system 400 (e.g., based on input from a subject matter expert) and/or assigned based on user input from an end user, among other possibilities.

FIG. 9A depicts an example GUI screen 900 that may be displayed by an output system 108 in accordance with instructions from the analytics system 400, which is a "Fleet View" screen that includes a list of assets in a fleet along with a set of sortable, filterable columns showing relevant information about the assets.

As shown in FIG. 9A, this GUI screen 900 includes an "Operational Guidance" column 902 showing a current recommended operating mode for each asset in the fleet, along with color coding to more clearly illustrate the different levels of recommended operating modes. (As shown, the "Operational Guidance" column may simply be blank for an asset if there is no failure type predicted to occur at the asset in the foreseeable future and thus no recommended operating mode assigned.) In some embodiments, it may also be possible to filter and/or sort assets using the "Operational Guidance" column 902, which may allow a user to focus in on assets that fall into a particular category of recommended operating mode. Additionally, as shown, the GUI screen 902 may include a "Failure Mode" column 904 showing the identified failure type that corresponds to each asset's recommended operating mode, which may be the identified failure type at an asset that is deemed to have the highest categorization level. (As shown, the "Failure Mode" column may simply be blank for an asset if there is no failure type predicted to occur at the asset in the foreseeable future. The GUI screen 902 may include various other columns as well, examples of which include a number of pending faults, data last logged, location, work items, and model number.

As further shown in FIG. 9A, the GUI screen 900 may also include a "Summary" panel 906 that provides summary-level information for the fleet of assets. In one implementation, this summary panel 906 may include a graphical indicator 908 that shows how many assets within fleet fall into each different category of recommended operating mode. For instance, the graphical indicator 908 may take the form of a horizontal bar that is broken into different color-coded segments corresponding to the different types of recommended operating mode, where the size of each recommended operating mode's respective segment indicates an extent of assets in the fleet that have been assigned the particular type of recommended operating mode. In the graphical indicator 908 of FIG. 9A, for example, there is a first segment 910 that represents an extent of assets in the fleet having a recommended operating mode of "Inoperable," a second segment 912 represents an extent of assets in the fleet having a recommended operating mode of "Trail Only," a third segment 914 that represents an extent of assets in the fleet having a recommended operating mode of "Limited Use," and a fourth segment 916 that represents an extent of assets in the fleet having either a recommended operating mode of "Full Operation" or no assigned operating mode. The summary panel 906 of the GUI screen 900 may also include other types of summary-level information for the fleet, examples of which include a total number of assets in the fleet, a total number of pending faults for the fleet, and a total number of open work items for the fleet.

Although not shown, another GUI screen that may be displayed by an output system 108 in accordance with instructions from the analytics system 400 may take the form of a "Map" view, which may show the location of certain assets on a geographical map using icons that are color-coded to reflect the recommended operating modes of the assets.

The recommended operating mode of the given asset may be included in various other GUI screens and/or presented to a user in various other manners well.

As another possibility, the analytics system 400 may use the given asset's recommended operating mode as a basis for generating and sending an alert to an output system 108. For instance, if the recommended operating mode for the given asset is determined to be of a particular type (e.g., an "Inoperable" mode), the analytics system 400 may be configured to cause an output system 108 to display an alert indicating an undesirable change in the given asset's recommended operating mode.

As yet another possibility, the analytics system 400 may use the given asset's recommended operating mode as a basis for generating a list of one or more recommended actions that may help improve the operating state of the given asset and then causing an output system 108 to output an indication of the recommended actions.

As still another possibility, the analytics system 400 may use the given asset's recommended operating mode as a basis for generating and sending an instruction to a work-order system and/or a parts-ordering system.

As a further possibility, the analytics system 400 may use the given asset's recommended operating mode as a basis for generating and sending one or more commands to the given asset that facilitate modifying the given asset's operation in a manner that improves its operating state.

The analytics system 400 may use the recommended operating mode of the given asset as a basis for carrying out other actions as well.

F. Subsystem Health Metrics

As suggested above, in some implementations, the analytics system 400 may be configured to determine one or more subsystem-level health metric. Specifically, the analytics system 400 may be configured to determine a subsystem-level health metric as a standalone health metric and/or multiple subsystem-level health metrics that may be utilized to determine an asset-level health metric. A given subsystem health metric may indicate a single, aggregated parameter that reflects whether a failure will occur at the particular subsystem of the given asset within a certain period of time into the future.

Generally, a subsystem-level health metric may be determined in a manner similar, at least in some respects, to the operations discussed with reference to FIGS. 5A and 5B. However, some of the operations may be modified, or are perhaps unnecessary, in determining a subsystem-level health metric or additional operations may be utilized.

In particular, in some implementations, at block 502, the set of failures may include failures that could render the particular subsystem inoperable if they were to occur. In some cases, the set of failures may be defined from abnormal-condition indicators, such as fault codes, associated with a subsystem. In general, a subsystem may have one or multiple indicators associated with it. For example, Fault Codes 1-3 of FIG. 3 may all be associated with a given subsystem 202. The data science system 404 may determine the indicators associated with the given subsystem 202 in a number of manners.

In some examples, the abnormal-condition indicators associated with the given subsystem 202 may be user defined. In particular, the data science system 404 may receive an indication of the given subsystem 202 and indicators associated with the given subsystem 202, perhaps from an output system 108 that received inputs from a user.

In other examples, the data science system 404 may be configured to determine the abnormal-condition indicators associated with the given subsystem 202. This operation may be based on historical data stored in the databases 406 and/or external data provided by the data sources 110.

For instance, historical repair data may be utilized. Based on such data, the data science system 404 may be configured to determine instances when the given subsystem 202 was repaired (e.g., a time and/or date of the repair). Based on that determination, the data science system 404 may then determine from the historical operating data any abnormal-condition indicators that were triggered before the repair. In other examples, the data science system 404 may instead determine from the historical operating data only those abnormal-condition indicators that were triggered before and then no longer triggered after the repair. In any event, the determined indicators may then be associated with the given subsystem 202.

In yet another example, the data science system 404 may be configured to determine abnormal-condition indicators associated with the given subsystem 202 by determining relevant sensors, which are sensors associated with the given subsystem 202, and then determining indicators associated with the relevant sensors. In some cases, the data science system 404 may determine the relevant sensors based on sensor attributes, such as sensor location on the asset 200 and/or sensor type (e.g., the physical property the sensor is configured to measure). For example, the data science system 404 may be configured to determine sensors that are physically located on or within the given subsystem 202. Additionally or alternatively, the data science system 404 may be configured to determine sensors that are in proximity to the given subsystem 202, such as sensors downstream or upstream of the given subsystem 202.

Further, the data science system 404 may be configured to determine sensors that are located on or within subsystems that affect the operation of the given subsystem 202. For instance, the data science system 404 may be configured to determine subsystems from which the given subsystem 202 receives inputs and/or subsystems to which the given subsystem 202 provides outputs. Or subsystems whose operating conditions are modified by the given subsystem 202 and/or subsystems that modify the operating conditions of the given subsystem 202. For example, the data science system 404 may determine that the sensors on an air-intake subsystem that operates to reduce operating temperatures of an engine subsystem are relevant to the engine subsystem.

In any event, after the data science system 404 determines the relevant sensors, the data science system 404 may be configured to determine any abnormal-condition indicators whose sensor criteria include measurements from the relevant sensors. These determined indicators then would be associated with the given subsystem 202 and used to identify the past occurrences of failures at block 504.

Another example operation that may differ in some respects to the subsystem-level health metric context is with respect to block 510. In particular, when determining an asset-level health metric from multiple subsystem-level health metrics, the data science system 404 may be configured to combine the multiple health metrics in a number of manners, some of which may be similar in some respects to the methods of combining failure models discussed above. In some implementations, the data science system 404 may be configured to weight each subsystem health metric equally or to weight certain subsystem-level health metrics different than others, which may be based on the subsystem.

The weighting may be based on the relative importance of a subsystem relative to the overall operation of the asset. For example, Subsystem A might have a health metric of 75% and Subsystem B might have a health metric of 85%. Weighting each subsystem health metric equally in determining an asset-level health metric might result in a health metric of 80%. On the other hand, assuming Subsystem A is determined to be three times more important than Subsystem B, weighting each subsystem health metric according to the subsystems' relative importance might result in a health metric of 77.5%. Other examples are also possible.

In any event, similar to the asset-level health metrics, the analytics system 400 may be configured to trigger a number of actions based on a subsystem health metric. However, the triggered actions may be more granular than those triggered based on an asset-level health metric. In particular, any of the actions discussed above may be directed to the given subsystem or a component thereof.

Moreover, subsystem-level health metrics may allow the analytics system 400 to more quickly identify sensor measurements that suggest a failure might occur in the future. Accordingly, when determining a subsystem-level health metric, the analytics system 400 might be configured to forecast for a smaller window of time than in the asset-level health metrics, thereby providing a more useful prediction. For instance, while an asset-level health metric might have a resolution of a first amount of time with a particular degree of accuracy (e.g., the asset-level health metric may indicate a probability that no faults will occur in the next two weeks), a subsystem-level health metric may have a resolution of a second, smaller amount of time with the same degree of accuracy (e.g., the subsystem-level health metric may indicate a probability that no faults will occur in the next week). Other advantages of subsystem-level health metrics are also possible.

In a further aspect, the analytics system 400 may be configured to use a given collection of individual failure models (i.e., a health-metric model) for a given subsystem of an asset to determine a recommended operating mode of the given subsystem using a process that is similar to the one described above for determining an asset-level recommended operating mode. Once such a system-level recommended operating mode is determined, the analytics system 400 may also use a subsystem-level recommended operating mode for an asset in a manner that is similar to how the analytics system 400 may use an asset-level predicted operating data for the asset. In this respect, as one possible example, the analytics system 400 may facilitate causing one or more of the output systems 108 to display one or more subsystem-level recommended operating modes for a given asset, perhaps together with an asset-level recommended operating mode for the asset.

Figure 9B:
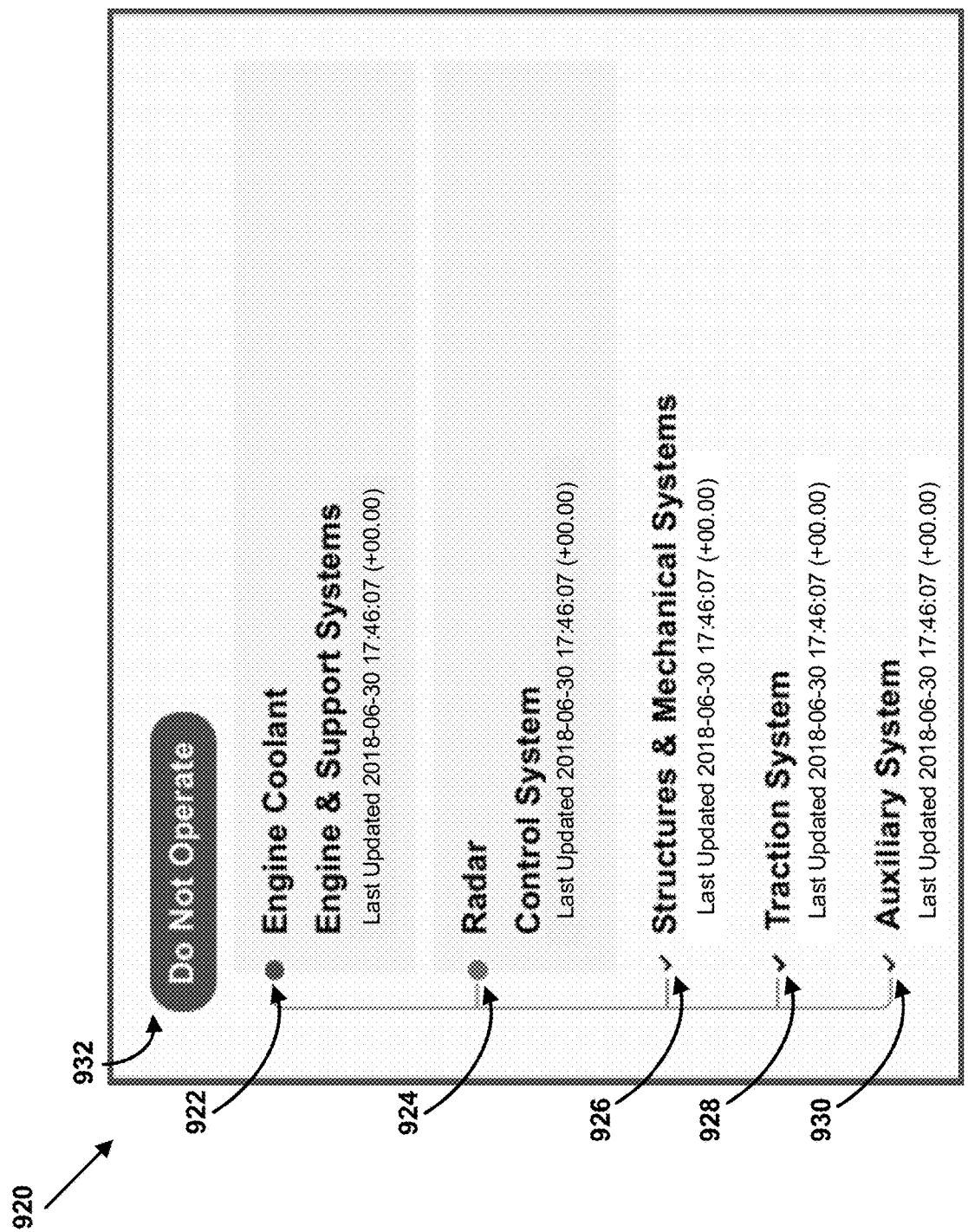
FIG. 9B depicts an example graphical user interface screen showing a subsystem-level recommended operating mode for an asset.

FIG. 9B depicts one possible example of a GUI screen 920 that shows a subsystem-level recommended operating mode (or the absence thereof) for each of a plurality of subsystems of a given asset. For instance, the GUI screen 920 shows (1) a first indicator 922 for an asset's "Engine Coolant" subsystem that is in the form of a circle having a first color, which indicates that the recommended operating mode for the subsystem is "Do Not Operate," (2) a second indicator 924 for the asset's "Radar" subsystem that is in the form of a circle having a second color, which indicates that the recommended operating mode for the subsystem is "Limited Use," (3) indicators 926, 928, and 930 for the asset's "Structures & Mechanical Systems," "Traction System," and "Auxiliary System" subsystems that are each in the form of a check mark, which indicates that there is no recommended operating mode for these subsystem (i.e., there is no failure type predicted to occur at these subsystems in the foreseeable future). In addition, the GUI screen 920 also includes a representation 932 of an asset-level recommended operating mode for the asset, which in this example is "Do Not Operate." As shown, the representation 932 may have the same color as the indicator 922 showing that the "Engine Coolant" subsystem has a subsystem-level recommended operating model of "Do Not Operate."

A GUI screen for displaying subsystem-level recommended operating mode may take various other forms as well.

In an embodiment where the analytics system 400 determines respective subsystem-level recommended operating modes for multiple different subsystems of an asset, the analytics system 400 may also be configured to use these subsystem-level recommended operating modes as a basis for determining an asset-level recommended operating mode. For example, once an asset's multiple subsystem-level recommended operating modes are determined, the analytics system 400 may select one of the multiple subsystem-level recommended operating modes (e.g., the subsystem-level recommended operating mode for the most concerning subsystem) to use as an asset-level recommended operating mode. In other words, in such an example, the asset's multiple subsystem-level recommended operating modes may be "rolled up" into an asset-level recommended operating mode.

G. Updating Health Metric Module Based on Feedback

In another aspect, the analytics system 400 may be configured to receive feedback data regarding an action triggered based on a health metric, and then based on the feedback data, update the health-metric model and/or actions triggered based on health metrics (collectively referred to herein as the "health metric module").

This feedback data may take various forms, but in general, the feedback data may indicate a status of an action triggered based on health metric data. Examples of this status may be that the action was acted upon, that the action was performed and successfully corrected an impending failure, that the action was performed but did not correct an issue, or that the action was not feasible, among other examples. Further, the analytics system 400 may receive this feedback data from various sources, examples of which include a user operated output device or system.

In a particular example, based on a health metric, the analytics system 400 may have triggered generating a work order to repair a particular component of a given asset. After completing the work order, the mechanic may utilize a client device of an output system 108 to provide feedback regarding the actions taken in response to the work order, such as an indication that the particular component indeed needed to be fixed and/or that the repair was performed successfully or that the particular component did not need to be fixed and/or the repair could not be performed. The analytics system 400 may receive this feedback data and then use it to update the health metric module in various manners.

For instance, the analytics system 400 could refine the health metric module based on this feedback data. Specifically, the feedback data may cause the analytics system 400 to add or remove a failure to or from the set of failures from block 502 of FIG. 5A, modify a weight applied to an output of a given failure model, and/or adjust a particular predictive algorithm utilized to predict a likelihood of a given failure occurring, among other examples. In another instance, the analytics system 400 may update the health metric module so as to prioritize a type of action over others if the health metric falls below a health threshold in the future. Many other examples are possible as well.

In another example of feedback data, the analytics system 400 may have caused an output system 108 to display an indication of a list of recommended routes for a given asset to take that may help increase (or at least maintain) the health metric (e.g., routes with few elevation changes and/or climbs). Thereafter, the analytics system 400 may receive feedback data indicating that a recommended route is not feasible because of construction on the route. Based on such feedback, the analytics system 400 may remove the recommended route from the list of recommended routes. Other examples are also possible.

I. Historical Health Metrics

The analytics system 400 may be configured to store health metric data corresponding to the assets 102 in the databases 406. The analytics system 400 may do so for a plurality of assets over time. From such historical health metric data, the analytics system 400 may be configured to perform a number of operations.

Figure 10:
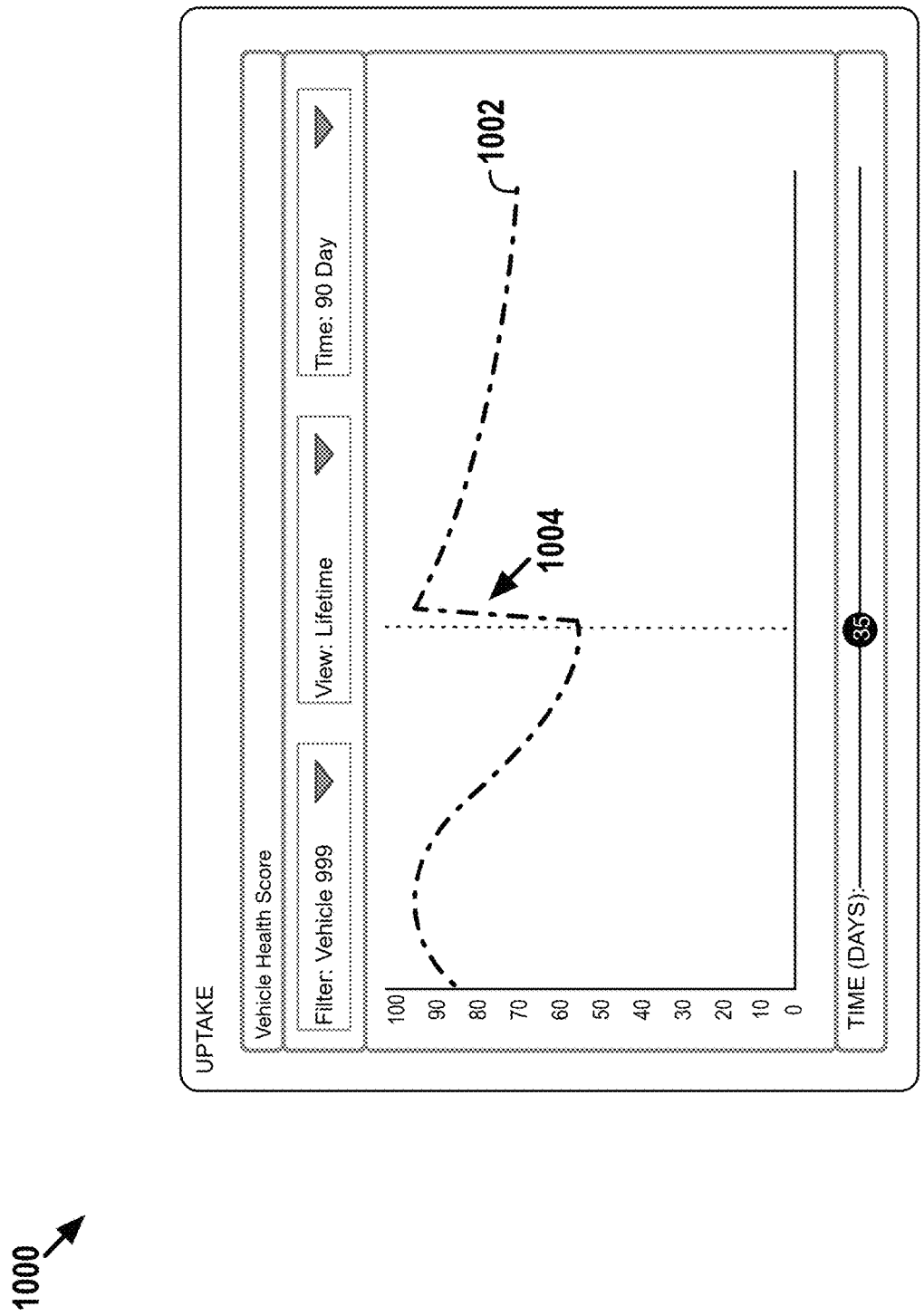
FIG. 10 depicts an example graphical user interface screen showing a representation of a historical health score.

In one example, the analytics system 400 may be configured to provide historical health metric data to one or more of the output systems 108, which may then display a graphical representation of the health metric. FIG. 10 depicts an example GUI screen 1000 showing a representation of a health metric over time that may be displayed by an output system 108. As shown, the GUI screen 1000 includes a health-metric curve 1002 that is shown for an example period of time (e.g., 90-day period of time). In this example, a sharp change 1004 in the health metric occurred around thirty-five days into the example period of time, which may indicate that a repair occurred to the asset 200 at that time. Other example representations of health metrics over time are also possible.

In another example, based at least on historical health metric data, the analytics system 400 may be configured to identify variables that influence health metrics. For instance, the analytics system 400 may be configured to analyze historical health metric data to identify variables associated with assets whose health metrics are relatively high (or relatively low). Examples of variables that may influence health metrics may include asset variables that indicate characteristics of a given asset and the operation thereof, operator variables that indicate characteristics of the human operators that operate a given asset, and maintenance variables that indicate characteristics of mechanics and the like that perform routine maintenance or repairs to a given asset, among other examples.

Examples of asset variables may include asset brand, asset model, asset travel schedules, asset payloads, and asset environment, among others. Asset brand may indicate the manufacturer of a given asset, while asset model may indicate the particular model of asset from the given manufacturer (e.g., a model identifier or the like). Asset travel schedules may indicate routes that a given asset traverses, which may include an indication of elevations, terrain, and/or travel durations. Asset payloads may indicate type and/or amount (e.g., weight) of cargo or the like that an asset hauls. Asset environment may indicate various characteristics about the environment in which a given asset is operated, such as geospatial location, climate, average ambient temperature or humidity, and/or proximity of sources of electrical interference, among other examples.

Examples of operator variables may include any variable associated with the person or persons that operate an asset, such as an operator identifier, operator schedule, and operator habits, among others. An operator identifier may identify the individual operator that operated a given asset. An operator schedule may indicate the type of shift (e.g., morning, day, night, etc.) or duration of shift (e.g., number of hours) during which a given asset is operated. Operator habits may indicate various trends in an operator's handling of a given asset, such as average braking distance, average acceleration time, average deceleration time, average RPMs, and the like.

Examples of maintenance variables may include any variable associated with the maintenance (e.g., general upkeep and/or review of operating conditions of an asset) and/or repair of an asset, such as date of maintenance or repair, time between asset checkups, location of repair, repair-shop identifier, mechanic identifier, and duration of repair time, among others. Date of maintenance or repair may indicate the date as well as time that maintenance or a repair was performed on a given asset. Time between checkups may indicate an amount of time between instances when maintenance personnel evaluated the asset for any operating problems. Location of repair may indicate where a repair was performed (e.g., at a repair shop or out in the field). Repair-shop identifier may identify the particular repair-shop or the like that repaired a given asset, while mechanic identifier may identify the particular mechanic or the like that worked on the given asset. Duration of repair time may indicate the amount of time that was spent repairing a given asset.

One of ordinary skill in the art will appreciate that the aforementioned asset-related variables are provided for purposes of example and explanation only and are not meant to be limiting. Numerous other variables are possible and contemplated herein.

In practice, the analytics system 400 may be configured to determine variables based in part on asset-related historical data stored in the databases 406 or provided by the data sources 110. Examples of such data may include manufacturer or asset technical specifications, asset travel logs, asset payload logs, weather records, maps, building electricity bills, operator time cards or the like, operator work schedules, asset operating data, maintenance or repair logs, mechanic time cards, or any other data discussed herein, among other examples.

Figure 11:
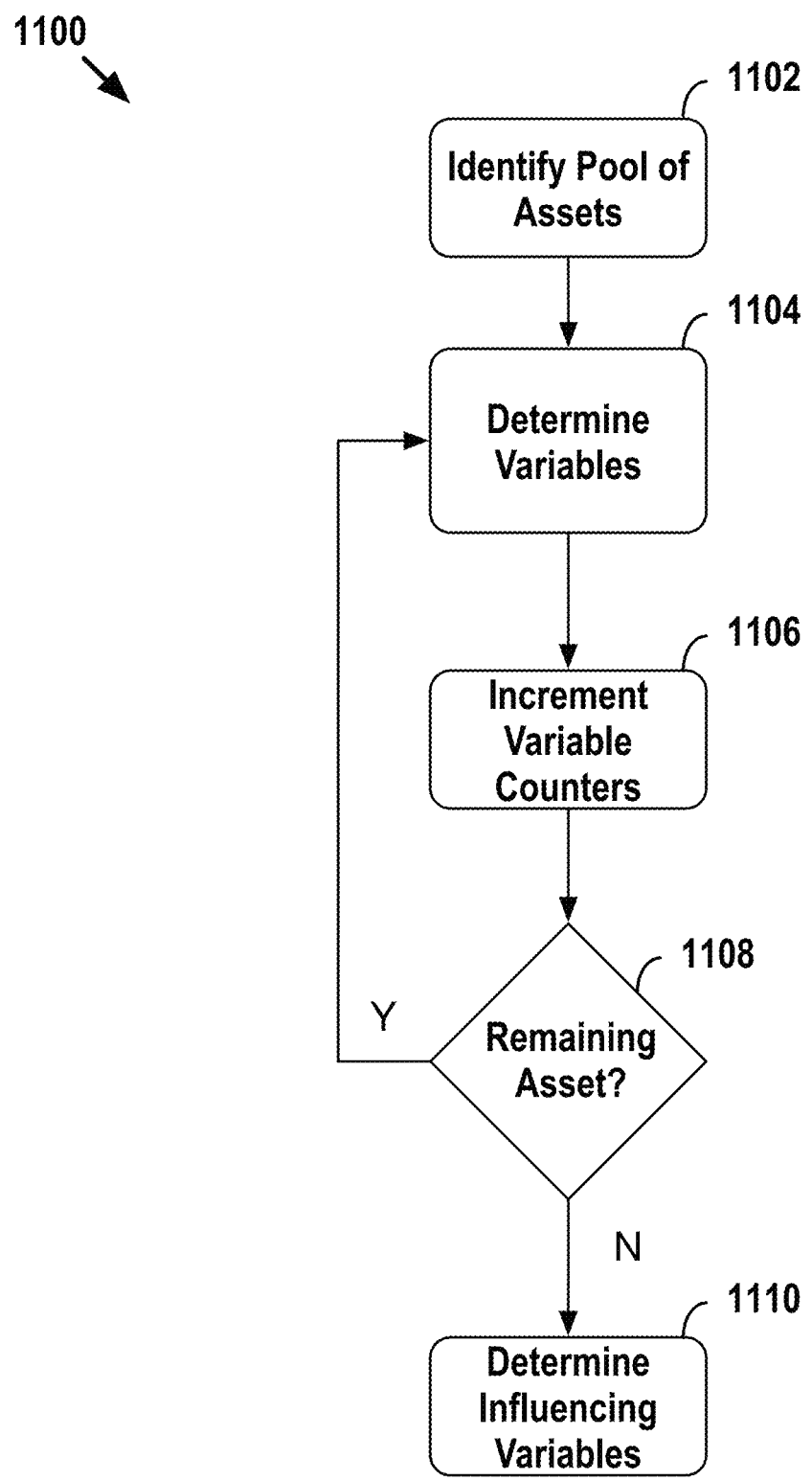
FIG. 11 depicts an example flow diagram for determining variables.

The analytics system 400 may be configured to determine variables based on historical health-metric data, and perhaps other historical asset-related data, in a number of manners. FIG. 11 depicts an example flow diagram 1100 for determining variables.

As shown, at block 1102, the analytics system 400 may be configured to identify one or more assets (collectively referred to herein as a "pool of assets") whose health metrics over time will be analyzed. In some examples, the pool of assets may include assets with relatively high health metrics. For instance, the asset pool may include each asset whose historical health metric has been above a threshold value for a particular amount of time, whose historical health metric has never dropped below a threshold value, or whose average historical health metric determined over a particular amount of time is above a threshold value, among other possibilities. In other instances, the asset pool may include a particular number of assets whose health metrics meet any of the aforementioned threshold requirements. On the other hand, in other examples, the pool of assets may include assets with relatively low health metrics.

At block 1104, for each asset in the pool of assets, the analytics system 400 may be configured to analyze the given asset's historical health-metric data and/or asset-related data to determine variables of the given asset. The analytics system 400 may do so for a given amount of time or over the whole operating life of each asset.

In practice, the analytics system 400 may be configured to determine any or all of the variables discussed above for the given asset, or the analytics system 400 may be configured to make this determination for a select subset of the variables, such as only asset attributes or only maintenance attributes, among other examples. The subset of the variables may be predefined and stored in a database 406 or dynamically determined, among other examples.

In some implementations, the analytics system 400 may be configured to determine the subset of variables based at least on the given asset's historical health-metric data. In particular, the analytics system 400 may be configured to identify trends in the given asset's historical health-metric data and determine a potential cause or causes of such a trend, perhaps from the historical asset-related data. In some cases, a trend may be a threshold amount of change (e.g., an increase or decrease) in a health metric over a certain period of time, a constant health metric for a certain amount of time, or a certain amount of increase followed by a certain amount of time prior to a threshold amount of decrease, among other examples.

In a specific example, the analytics system 400 may be configured to identify a threshold amount of increase in a historical health metric, such as an at least 10% increase, over a given period of time, such as a week. The analytics system 400 may then identify a time at which the trend began (or ended or a time in between) and analyze the asset-related data from around (e.g., a certain amount of time's worth of data before or after) the identified time to determine one or more potential causes of the change.

For instance, returning to FIG. 10, the analytics system 400 may evaluate the historical health-metric data represented by the health-metric curve 1002 and determine that the sharp change 904 is greater than a 10% increase in the health metric. The analytics system 400 may then identify the date corresponding to day 35 (e.g., May 1, 2015) shown on the GUI screen 1000 and based on various asset-related data, determine any events that took place around that May 1st date, which may indicate one or more potential causes of the sharp change 1004. In one example, the analytics system 400 may determine from repair logs that, on May 5, 2015, Mechanic A at Repair Shop 1 repaired the given asset's engine. Identifiers for Repair Shop 1 and Mechanic A may then become variables.

At block 1106, the analytics system 400 may generate a record of the determined variables. In examples, the analytics system 400 may store in one of the databases 406 variable counters for each of the variables. The analytics system 400 may be configured to increment the appropriate counters corresponding to each of the determined variables. The variable counters may provide an indication of the variables that are commonly found amongst assets with relatively high health metrics.

At block 1108, the analytics system 400 may then determine whether there are any remaining assets from the pool of assets for which variables should be determined and incremented. In the event that an asset remains, the analytics system 400 may repeat the loop of blocks 1104-1108. After the analytics system 400 has determined and incremented the variables for each of assets from the asset pool, the resulting data may then provide, to some degree, an indication of variables that lead to high health metrics.

FIG. 12 depicts conceptual illustrations of data that results from incrementing variable counters. In particular, histogram 1200 depicts counters for a maintenance variable for the pool of assets. More specifically, the histogram 1300 shows that more assets repaired by Mechanic A had high health metrics than assets repaired by Mechanics B and C. Histogram 1202 depicts counters for an asset environment variable, and in particular, that fewer assets had high health metrics that operated in an environment with ambient temperatures over 45° C. than any other temperature range. Histogram 1204 depicts counters for an operator habit variable and in particular, that more assets whose operator's average acceleration time was between ten and fifteen minutes had high health metrics than other acceleration times. Histogram 1206 depicts a counter for an asset variable that indicates that more assets of the type Brand A Model 7 had high health metrics than the other two model types. One of ordinary skill in the art will appreciate that these are but a few example variables and that numerous other variables are possible.

Returning to FIG. 11, at block 1110, the analytics system 400 may be configured to determine influencing variables based in part on the variable counters. In some examples, the influencing variables are variables whose variable counters exceed a predetermined threshold value. In other examples, the influencing variables are variables whose variable counters have a maximized value. For instance, referring to the histogram 1200, Mechanic A may be determined to be an influencing variable because the variable counter for Mechanic A has the highest value of the other counters. Other examples are also possible.

The analytics system 400 may determine influencing variables in a variety of other manners. For example, in other implementations, the analytics system 400 may determine influencing variables by first determining a pool of assets in line with block 1102 of FIG. 12 and then analyzing asset-related data for each of the assets from the pool of assets. The analytics system 400 may identify variables that the assets from the pools of assets have in common. These identified variables may then be defined as the influencing variables or a subset of the identified variables may be defined as the influencing variables (e.g., those variables that a threshold number of assets from the pool of assets have in common). Other manners for determining influencing variables are also possible.

After determining the influencing variables, the analytics system 400 may be configured to perform a number of operations. For example, the analytics system 400 may be configured to determine various recommendations with respect to assets, perhaps determining a ranked list of recommendations, and then cause a graphical display to output an indication of such recommendations to a user. In general, a given recommendation may be a general recommendation (e.g., a fleet-wide recommendation), such as that all assets should be operated at less than 75% capacity, or an asset- or asset-group-specific recommendation, such as that particular assets should be sent to a certain repair shop to get a specific repair performed.

Moreover, a given recommendation may be based on determining that a particular asset has a relatively low health metric and then evaluating variables of the particular asset. The given recommendation may then facilitate modifying the variables of the particular asset to more closely align with the influencing variables determined at block 1110.

Example recommendations may include recommended brands or models of assets to purchase, recommended repair shops or individual mechanics for future repairs, recommended repair schedules for one or more assets, recommended operators for future work shifts, recommended instructions for teaching operators to efficiently operate assets, and recommended location or environment to operate an asset, among other examples.

In other examples, the analytics system 400 may be configured to transmit an operating command to an asset that facilitates causing the asset to be operated in accordance with an influencing variable. For example, from the variable data represented graphically by the histogram 1204, the analytics system 400 may transmit instructions to assets where the instructions restrict how quickly the assets may be accelerated thereby bringing the operation of the assets closer to the average 10-15 minute acceleration time. Other examples are also possible.

Additionally or alternatively, the analytics system 400 may be configured to perform other operations based on historical health-metric data. In one example, the analytics system 400 may be configured to modify a health-metric module. Specifically, the analytics system 400 may trigger the generation of a work order based on a health metric reaching a particular threshold value. Thereafter, the analytics system 400 may then monitor the health metric data for a threshold amount of time. In the event that the health metric increases a certain amount within a predetermined amount of time after generating the work order, the analytics system 400 may be configured to infer that the work order to repair the particular component was performed and fixed the cause of the declining health metric. Based on this inference, the analytics system 400 may be configured to modify a health-metric model and/or actions triggered based off the health-metric model. Other examples are also possible.

The analytics system 400 may also may be configured to determine influencing variables based on historical recommended operating mode data in a similar manner.

V. Conclusion

To the extent that examples described herein involve operations performed or initiated by actors, such as "humans", "operators", "users" or other entities, this is for purposes of example and explanation only. The claims should not be construed as requiring action by such actors unless explicitly recited in the claim language.

What is claimed is:

1. A computing system comprising:
a network interface configured to interface the computing system with a communication network;
at least one processor;
a non-transitory computer-readable medium; and
program instructions stored on the non-transitory computer-readable medium that are executable by the at least one processor to cause the computing system to:
receive sensor data for a sensor-equipped asset, wherein the sensor data indicates operating conditions for the sensor-equipped asset;
input the sensor data for the sensor-equipped asset into a plurality of individual failure models for a group of failure types, wherein each individual failure model functions to (1) receive the sensor data for the sensor-equipped asset as input and (2) output a respective value indicating a likelihood of a respective failure type occurring at the sensor-equipped asset within a future period of time, wherein the individual failure model for each respective failure type in the group comprises a machine learning model that was defined by applying a machine learning technique to sensor data corresponding to instances of the respective failure type that occurred at assets in the past;
based on the respective value output by each of the plurality of individual failure models for the group of failure types, determine that two or more different failure types are predicted to occur at the sensor-equipped asset;
identify a respective categorization of each of the two or more different failure types, wherein identifying the respective categorization of each of the two or more different failure types results in an identification of at least two different categorization levels along a preestablished scale of categorization levels;
based on the respective categorization of each of the two or more different failure types, determine one particular recommended operating mode of the sensor-equipped asset that comprises a recommendation of a particular capacity in which the sensor-equipped asset should be used during the future period of time, wherein determining the one particular recommended operating mode comprises:
using preestablished criteria to select, from the at least two different categorization levels along the preestablished scale of categorization levels, one single categorization level that serves as a representative categorization for the two or more different failure types, wherein the one single categorization level corresponds to one single recommended operating mode along a preestablished scale of recommended operating modes; and
identifying the one single recommended operating mode that corresponds to the one single categorization level as the one particular recommended operating mode of the sensor-equipped asset; and
cause a computing device to display a visual representation of the one particular recommended operating mode of the sensor-equipped asset.

2. The computing system of claim 1, wherein the plurality of individual failure models are included as part of a health-metric model that comprises a predefined collection of individual failure models.

3. The computing system of claim 1, wherein the program instructions that are executable by the at least one processor to cause the computing system to determine that the two or more different failure types are predicted to occur at the sensor-equipped asset comprise program instructions stored on the non-transitory computer-readable medium that are executable by the at least one processor to cause the computing system to:
for each of the plurality of individual failure models, compare the respective value indicating the likelihood of the respective failure type occurring at the sensor-equipped asset to a threshold value and determine that the respective failure type is predicted to occur if the respective value indicating the likelihood meets the threshold value.

4. The computing system of claim 1, wherein the at least two different categorization levels along the preestablished scale of categorization levels comprises (a) at least two severity levels along a preestablished scale of severity levels, (b) at least two safety levels along a preestablished scale of safety levels, or (c) at least two compliance levels along a preestablished scale of compliance levels.

5. The computing system of claim 1, wherein the at least two different categorization levels along the preestablished scale of categorization levels comprises at least two different severity levels along a preestablished scale of severity levels, and wherein using the preestablished criteria to select, from the at least two different categorization levels along the preestablished scale of categorization levels, the one single categorization level that serves as the representative categorization for the two or more different failure types comprises:

selecting, from the at least two different severity levels along the preestablished scale of severity levels, whichever severity level is most severe.

6. The computing system of claim 1, wherein identifying the one single recommended operating mode that corresponds to the one single categorization level comprises:
identifying the one single recommended operating mode that corresponds to the one single categorization level based on preestablished data that defines a correlation between categorization levels and recommended operating modes.

7. The computing system of claim 6, wherein the preestablished data that defines a correlation between categorization levels and recommended operating modes comprises data that was previously established based on user input.

8. The computing system of claim 1, wherein the one particular recommended operating mode comprises one of (a) a recommendation not to use the sensor-equipped asset in any capacity, (b) a recommendation to use the sensor-equipped asset only in a limited capacity, or (c) a recommendation to use the sensor-equipped asset at full capacity.

9. The computing system of claim 1, further comprising program instructions stored on the non-transitory computer-readable medium that are executable by the at least one processor to cause the computing system to:
based on the determination of the one particular recommended operating mode, carry out a remedial action that comprises one or more of (a) causing a computing device to output an alert indicating that the one particular recommended operating mode has been determined for the sensor-equipped asset, (b) causing a computing device to output an indication of one or more recommended repairs to the sensor-equipped asset, (c) causing the sensor-equipped asset to modify its operation, or (d) transmitting, to a parts-ordering system, part-order data to facilitate causing the parts-ordering system to order a component of the sensor-equipped asset.

10. A non-transitory computer-readable storage medium, wherein the non-transitory computer-readable storage medium is provisioned with software that is executable to cause a computing system to perform functions including:
receiving sensor data for a sensor-equipped asset, wherein the sensor data indicates operating conditions for the sensor-equipped asset;
inputting the sensor data for the sensor-equipped asset into a plurality of individual failure models for a group of failure types, wherein each individual failure model functions to (1) receive the sensor data for the sensor-equipped asset as input and (2) output a respective value indicating a likelihood of a respective failure type occurring at the sensor-equipped asset within a future period of time, wherein the individual failure model for each respective failure type in the group comprises a machine learning model that was defined by applying a machine learning technique to sensor data corresponding to instances of the respective failure type that occurred at assets in the past;
based on the respective value output by each of the plurality of individual failure models for the group of failure types, determining that two or more different failure types are predicted to occur at the sensor-equipped asset;
identifying a respective categorization of each of the two or more different failure types, wherein identifying the respective categorization of each of the two or more different failure types results in an identification of at least two different categorization levels along a preestablished scale of categorization levels;
based on the respective categorization of each of the two or more different failure types, determining one particular recommended operating mode of the sensor-equipped asset that comprises a recommendation of a particular capacity in which the sensor-equipped asset should be used during the future period of time, wherein determining the one particular recommended operating mode comprises:
using preestablished criteria to select, from the at least two different categorization levels along the preestablished scale of categorization levels, one single categorization level that serves as a representative categorization for the two or more different failure types, wherein the one single categorization level corresponds to one single recommended operating mode along a preestablished scale of recommended operating modes; and
identifying the one single recommended operating mode that corresponds to the one single categorization level as the one particular recommended operating mode of the sensor-equipped asset; and
causing a computing device to display a visual representation of the one particular recommended operating mode of the sensor-equipped asset.

11. The non-transitory computer-readable storage medium of claim 10, wherein the plurality of individual failure models are included as part of a health-metric model that comprises a predefined collection of individual failure models.

12. The non-transitory computer-readable storage medium of claim 10, wherein determining that the two or more different failure types are predicted to occur at the sensor-equipped asset comprises:
for each of the plurality of individual failure models, comparing the respective value indicating the likelihood of the respective failure type occurring at the sensor-equipped asset to a threshold value and determining that the respective failure type is predicted to occur if the respective value indicating the likelihood meets the threshold value.

13. The non-transitory computer-readable storage medium of claim 10, wherein the at least two different categorization levels along the preestablished scale of categorization levels comprises (a) at least two severity levels along a preestablished scale of severity levels, (b) at least two safety levels along a preestablished scale of safety levels, or (c) at least two compliance levels along a preestablished scale of compliance levels.

14. The non-transitory computer-readable storage medium of claim 10, wherein the at least two different categorization levels along the preestablished scale of categorization levels comprises at least two different severity levels along a preestablished scale of severity levels, and wherein using the preestablished criteria to select, from the at least two different categorization levels along the preestablished scale of categorization levels, the one single categorization level that serves as the representative categorization for the two or more different failure types comprises:
selecting, from the at least two different severity levels along the preestablished scale of severity levels, whichever severity level is most severe.

15. The non-transitory computer-readable storage medium of claim 10, wherein identifying the one single recommended operating mode that corresponds to the one single categorization level comprises:

identifying the one single recommended operating mode that corresponds to the one single categorization level based on preestablished data that defines a correlation between categorization levels and recommended operating modes.

16. The non-transitory computer-readable storage medium of claim 10, wherein the one particular recommended operating mode comprises one of (a) a recommendation not to use the sensor-equipped asset in any capacity, (b) a recommendation to use the sensor-equipped asset only in a limited capacity, or (c) a recommendation to use the sensor-equipped asset at full capacity.

17. The non-transitory computer-readable storage medium of claim 10, wherein the software is executable to cause the computing system to perform further functions including:
- based on the determination of the one particular recommended operating mode, carrying out a remedial action that comprises one or more of (a) causing a computing device to output an alert indicating that the one particular recommended operating mode has been determined for the sensor-equipped asset, (b) causing a computing device to output an indication of one or more recommended repairs to the sensor-equipped asset, (c) causing the sensor-equipped asset to modify its operation, or (d) transmitting, to a parts-ordering system, part-order data to facilitate causing the parts-ordering system to order a component of the sensor-equipped asset.

18. A computer-implemented method comprising:
- receiving sensor data for a sensor-equipped asset, wherein the sensor data indicates operating conditions for the sensor-equipped asset;
- inputting the sensor data for the sensor-equipped asset into a plurality of individual failure models for a group of failure types, wherein each individual failure model functions to (1) receive the sensor data for the sensor-equipped asset as input and (2) output a respective value indicating a likelihood of a respective failure type occurring at the sensor-equipped asset within a future period of time, wherein the individual failure model for each respective failure type in the group comprises a machine learning model that was defined by applying a machine learning technique to sensor data corresponding to instances of the respective failure type that occurred at assets in the past;
- based on the respective value output by each of the plurality of individual failure models for the group of failure types, determining that two or more different failure types are predicted to occur at the sensor-equipped asset;
- identifying a respective categorization of each of the two or more different failure types, wherein identifying the respective categorization of each of the two or more different failure types results in an identification of at least two different categorization levels along a preestablished scale of categorization levels;
- based on the respective categorization of each of the two or more different failure types, determining one particular recommended operating mode of the sensor-equipped asset that comprises a recommendation of a particular capacity in which the sensor-equipped asset should be used during the future period of time, wherein determining the one particular recommended operating mode comprises:
  using preestablished criteria to select, from the at least two different categorization levels along the preestablished scale of categorization levels, one single categorization level that serves as a representative categorization for the two or more different failure types, wherein the one single categorization level corresponds to one single recommended operating mode along a preestablished scale of recommended operating modes; and
  identifying the one single recommended operating mode that corresponds to the one single categorization level as the one particular recommended operating mode of the sensor-equipped asset; and
- causing a computing device to display a visual representation of the one particular recommended operating mode of the sensor-equipped asset.

19. The computer-implemented method of claim 18, wherein the at least two different categorization levels along the preestablished scale of categorization levels comprises (a) at least two severity levels along a preestablished scale of severity levels, (b) at least two safety levels along a preestablished scale of safety levels, or (c) at least two compliance levels along a preestablished scale of compliance levels.

20. The computer-implemented method of claim 18, wherein the one particular recommended operating mode comprises one of (a) a recommendation not to use the sensor-equipped asset in any capacity, (b) a recommendation to use the sensor-equipped asset only in a limited capacity, or (c) a recommendation to use the sensor-equipped asset at full capacity.

* * * * *